(12) United States Patent
Nguyen et al.

(10) Patent No.: US 11,950,794 B2
(45) Date of Patent: Apr. 9, 2024

(54) ELECTRICALLY ENHANCED RETRIEVAL OF MATERIAL FROM VESSEL LUMENS

(71) Applicant: Covidien LP, Mansfield, MA (US)

(72) Inventors: Hoai (Kevin) Nguyen, Westminster, CA (US); Gaurav Girdhar, Ladera Ranch, CA (US); Andyanhdzung Huynh, Westminster, CA (US)

(73) Assignee: COVIDIEN LP, Mansfield, MA (US)

( * ) Notice: Subject to any disclaimer, the term of this patent is extended or adjusted under 35 U.S.C. 154(b) by 154 days.

(21) Appl. No.: 17/450,524

(22) Filed: Oct. 11, 2021

(65) Prior Publication Data

US 2022/0022900 A1 Jan. 27, 2022

Related U.S. Application Data

(62) Division of application No. 16/024,388, filed on Jun. 29, 2018, now Pat. No. 11,160,571.

(Continued)

(51) Int. Cl.
*A61B 17/12* (2006.01)
*A61B 17/22* (2006.01)
(Continued)

(52) U.S. Cl.
CPC ...... *A61B 17/221* (2013.01); *A61B 17/12109* (2013.01); *A61B 17/12136* (2013.01); *A61B 17/12168* (2013.01); *A61B 17/22031* (2013.01); *A61B 17/22032* (2013.01); *A61M 25/0021* (2013.01); *A61M 25/0105* (2013.01);
(Continued)

(58) Field of Classification Search
CPC .... A61M 2025/0042; A61M 2025/109; A61B 2018/0041; A61B 17/12022; A61B 17/12136; A61B 2017/12109
See application file for complete search history.

(56) References Cited

U.S. PATENT DOCUMENTS

| | | | |
|---|---|---|---|
| 5,549,626 | A | 8/1996 | Miller et al. |
| 5,885,278 | A | 3/1999 | Fleischman |

(Continued)

FOREIGN PATENT DOCUMENTS

| | | |
|---|---|---|
| CN | 101472685 A | 7/2009 |
| CN | 102753106 A | 10/2012 |

(Continued)

OTHER PUBLICATIONS

International Search Report and Written Opinion dated Mar. 24, 2022; International Application No. PCT/US2021/061540; 10 pages.

(Continued)

*Primary Examiner* — Laura A Bouchelle
(74) *Attorney, Agent, or Firm* — Fortem IP LLP; Matt Lincicum; Suzannah Beeman

(57) ABSTRACT

Retrieval of material from vessel lumens can be improved by electrically enhancing attachment of the material to the thrombectomy system. The system can include a catheter having a distal portion configured to be positioned adjacent to a thrombus in a blood vessel, an electrode disposed at the distal portion of the catheter, and an interventional element configured to be delivered through a lumen of the catheter. The electrode and the interventional element are each configured to be electrically coupled to an extracorporeal power supply.

15 Claims, 17 Drawing Sheets

Related U.S. Application Data

(60) Provisional application No. 62/688,636, filed on Jun. 22, 2018.

(51) Int. Cl.
  *A61B 17/221* (2006.01)
  *A61M 25/00* (2006.01)
  *A61M 25/01* (2006.01)
  *A61M 25/09* (2006.01)
  *A61M 25/10* (2013.01)
  *A61N 1/378* (2006.01)
  *A61B 17/00* (2006.01)

(52) U.S. Cl.
  CPC ........ *A61M 25/09* (2013.01); *A61M 25/1018* (2013.01); *A61N 1/378* (2013.01); *A61B 2017/00778* (2013.01); *A61B 2017/00929* (2013.01); *A61B 2017/22034* (2013.01); *A61B 2017/2215* (2013.01); *A61B 2217/005* (2013.01); *A61M 2025/0042* (2013.01); *A61M 2025/0166* (2013.01); *A61M 2025/09008* (2013.01); *A61M 2025/091* (2013.01); *A61M 2025/109* (2013.01)

(56) References Cited

U.S. PATENT DOCUMENTS

| | | |
|---|---|---|
| 5,928,260 A | 7/1999 | Chin et al. |
| 5,972,019 A | 10/1999 | Engelson et al. |
| 6,022,336 A | 2/2000 | Zadno-Azizi et al. |
| 6,059,779 A | 5/2000 | Mills |
| 6,315,794 B1 | 11/2001 | Richter |
| 6,540,733 B2 | 4/2003 | Constantz et al. |
| 6,658,288 B1 | 12/2003 | Hayashi |
| 6,663,650 B2 | 12/2003 | Sepetka et al. |
| 7,094,249 B1 | 8/2006 | Broome et al. |
| 7,520,966 B2 | 4/2009 | Diaz et al. |
| 7,556,624 B2 | 7/2009 | Laufer et al. |
| 8,032,222 B2 * | 10/2011 | Loushin ............ A61N 1/36007 607/40 |
| 8,038,674 B2 | 10/2011 | Schmaltz et al. |
| 8,246,641 B2 | 8/2012 | Osborne et al. |
| 8,382,821 B2 | 2/2013 | Richter |
| 8,603,014 B2 | 12/2013 | Alleman et al. |
| 8,795,305 B2 | 8/2014 | Martin et al. |
| 8,837,800 B1 | 9/2014 | Bammer et al. |
| 8,888,788 B2 | 11/2014 | Adams et al. |
| 8,965,534 B2 | 2/2015 | Hyatt et al. |
| 9,011,431 B2 | 4/2015 | Long et al. |
| 9,039,753 B2 | 5/2015 | Thramann |
| 9,119,656 B2 | 9/2015 | Bose et al. |
| 9,126,018 B1 | 9/2015 | Garrison |
| 9,179,971 B2 | 11/2015 | Kirschenman |
| 9,211,132 B2 | 12/2015 | Bowman |
| 9,241,699 B1 | 1/2016 | Kume et al. |
| 9,265,512 B2 | 2/2016 | Garrison et al. |
| 9,308,007 B2 | 4/2016 | Cully et al. |
| 9,399,118 B2 | 7/2016 | Kume et al. |
| 9,445,828 B2 | 9/2016 | Turjman et al. |
| 9,445,829 B2 | 9/2016 | Brady et al. |
| 9,492,637 B2 | 11/2016 | Garrison et al. |
| 9,539,022 B2 | 1/2017 | Bowman |
| 9,561,345 B2 | 2/2017 | Garrison et al. |
| 9,579,119 B2 | 2/2017 | Cully et al. |
| 9,585,741 B2 | 3/2017 | Ma |
| 9,642,635 B2 | 5/2017 | Vale et al. |
| 9,655,633 B2 | 5/2017 | Leynov et al. |
| 9,681,882 B2 | 6/2017 | Wilson et al. |
| 9,713,730 B2 | 7/2017 | Mathur et al. |
| 9,737,318 B2 | 8/2017 | Monstadt et al. |
| 9,770,251 B2 | 9/2017 | Bowman et al. |
| 9,795,400 B2 | 10/2017 | Davidson |
| 9,801,643 B2 | 10/2017 | Hansen et al. |
| 9,808,271 B2 | 11/2017 | Ulm |
| 9,827,084 B2 | 11/2017 | Bonnette et al. |
| 9,861,783 B2 | 1/2018 | Garrison et al. |
| 9,901,543 B2 | 2/2018 | Chausson et al. |
| 9,993,257 B2 | 6/2018 | Losordo et al. |
| 10,028,782 B2 * | 7/2018 | Orion ............... A61B 18/1492 |
| 10,029,008 B2 | 7/2018 | Creighton |
| 10,039,906 B2 | 8/2018 | Kume et al. |
| 10,092,241 B2 | 10/2018 | Toth et al. |
| 10,136,942 B1 | 11/2018 | Cosman |
| 10,251,569 B2 | 4/2019 | Burkett |
| 10,413,309 B2 | 9/2019 | Farhat et al. |
| 10,847,411 B2 | 11/2020 | Chen et al. |
| 10,874,411 B2 | 12/2020 | Nguyen et al. |
| 10,987,117 B2 | 4/2021 | Girdhar et al. |
| 11,058,444 B2 | 7/2021 | Girdhar et al. |
| 11,090,071 B2 | 8/2021 | Girdhar et al. |
| 11,160,571 B2 | 11/2021 | Nguyen et al. |
| 11,666,350 B2 | 6/2023 | Nguyen et al. |
| 2001/0001314 A1 | 5/2001 | Davison et al. |
| 2002/0059938 A1 | 5/2002 | Fogarty et al. |
| 2002/0091407 A1 | 7/2002 | Zadno-Azizi et al. |
| 2002/0133111 A1 | 9/2002 | Shadduck et al. |
| 2003/0088245 A1 | 5/2003 | Woloszko et al. |
| 2004/0219660 A1 | 11/2004 | Dev et al. |
| 2005/0096647 A1 | 5/2005 | Steinke et al. |
| 2006/0089638 A1 | 4/2006 | Carmel et al. |
| 2008/0042662 A1 | 2/2008 | Abraham |
| 2008/0045881 A1 | 2/2008 | Teitelbaum et al. |
| 2008/0262489 A1 | 10/2008 | Steinke et al. |
| 2008/0294181 A1 | 11/2008 | Wensel et al. |
| 2008/0300571 A1 * | 12/2008 | LePivert ............ A61M 25/1011 604/506 |
| 2009/0054918 A1 | 2/2009 | Henson |
| 2009/0069828 A1 | 3/2009 | Martin et al. |
| 2009/0198269 A1 | 8/2009 | Hannes et al. |
| 2009/0240250 A1 | 9/2009 | Hayashi et al. |
| 2009/0318892 A1 | 12/2009 | Aboytes et al. |
| 2009/0318943 A1 | 12/2009 | Eidenschink et al. |
| 2009/0318994 A1 | 12/2009 | Eidenschink et al. |
| 2010/0004623 A1 | 1/2010 | Hamilton et al. |
| 2010/0010533 A1 | 1/2010 | Burke et al. |
| 2010/0042136 A1 | 2/2010 | Berrada et al. |
| 2010/0168739 A1 | 7/2010 | Wu et al. |
| 2010/0174309 A1 | 7/2010 | Fulkerson et al. |
| 2010/0228280 A1 | 9/2010 | Groothuis et al. |
| 2010/0256616 A1 | 10/2010 | Katoh et al. |
| 2010/0256627 A1 | 10/2010 | Ma et al. |
| 2011/0196478 A1 | 8/2011 | Torosoff |
| 2011/0202085 A1 | 8/2011 | Loganathan et al. |
| 2011/0301549 A1 | 12/2011 | Hartmann |
| 2011/0301594 A1 | 12/2011 | Orion et al. |
| 2013/0008780 A1 | 1/2013 | Andreacchi et al. |
| 2013/0030461 A1 | 1/2013 | Marks et al. |
| 2013/0072960 A1 | 3/2013 | Schneider et al. |
| 2013/0184702 A1 | 7/2013 | Neal et al. |
| 2013/0281788 A1 | 10/2013 | Garrison |
| 2013/0282084 A1 | 10/2013 | Mathur et al. |
| 2013/0345739 A1 | 12/2013 | Brady et al. |
| 2014/0025069 A1 | 1/2014 | Willard et al. |
| 2014/0025152 A1 | 1/2014 | Headley |
| 2014/0172001 A1 | 6/2014 | Becking et al. |
| 2014/0188127 A1 | 7/2014 | Dubrul et al. |
| 2014/0276074 A1 | 9/2014 | Warner |
| 2014/0276778 A1 | 9/2014 | McLawhorn et al. |
| 2014/0277013 A1 | 9/2014 | Sepetka et al. |
| 2014/0277079 A1 | 9/2014 | Vale et al. |
| 2014/0309673 A1 | 10/2014 | Dacuycuy et al. |
| 2014/0309675 A1 | 10/2014 | Maisano et al. |
| 2014/0343595 A1 | 11/2014 | Monstadt et al. |
| 2014/0364896 A1 | 12/2014 | Consigny |
| 2015/0112321 A1 | 4/2015 | Cadouri |
| 2015/0133990 A1 | 5/2015 | Davidson |
| 2015/0150672 A1 | 6/2015 | Ma |
| 2015/0164666 A1 | 6/2015 | Johnson et al. |
| 2015/0182740 A1 | 7/2015 | Mickelsen |
| 2015/0230820 A1 | 8/2015 | Turjman et al. |
| 2015/0297251 A1 | 10/2015 | Sos |
| 2015/0359547 A1 | 12/2015 | Vale et al. |

(56) References Cited

U.S. PATENT DOCUMENTS

| | | |
|---|---|---|
| 2016/0008003 A1 | 1/2016 | Kleshinski et al. |
| 2016/0015402 A1 | 1/2016 | Brady et al. |
| 2016/0015935 A1 | 1/2016 | Chan et al. |
| 2016/0106448 A1 | 4/2016 | Brady et al. |
| 2016/0106449 A1 | 4/2016 | Brady et al. |
| 2016/0113663 A1 | 4/2016 | Brady et al. |
| 2016/0113665 A1 | 4/2016 | Brady et al. |
| 2016/0151618 A1 | 6/2016 | Powers et al. |
| 2016/0157843 A1 | 6/2016 | Dickson et al. |
| 2016/0157985 A1 | 6/2016 | Vo et al. |
| 2016/0199620 A1 | 7/2016 | Pokorney et al. |
| 2016/0228681 A1 | 8/2016 | Di Palma et al. |
| 2016/0228684 A1 | 8/2016 | Martin |
| 2016/0242661 A1 | 8/2016 | Fischell et al. |
| 2016/0296690 A1 | 10/2016 | Kume et al. |
| 2016/0302808 A1 | 10/2016 | Loganathan et al. |
| 2016/0331377 A1 | 11/2016 | Divino et al. |
| 2016/0375180 A1 | 12/2016 | Anzai |
| 2017/0079766 A1 | 3/2017 | Wang et al. |
| 2017/0079767 A1 | 3/2017 | Leon-Yip |
| 2017/0086862 A1 | 3/2017 | Vale et al. |
| 2017/0100143 A1 | 4/2017 | Grandfield |
| 2017/0105743 A1 | 4/2017 | Vale et al. |
| 2017/0164963 A1 | 6/2017 | Goyal |
| 2017/0215902 A1 | 8/2017 | Leynov et al. |
| 2017/0215955 A1 | 8/2017 | Hancock et al. |
| 2017/0224953 A1 | 8/2017 | Tran et al. |
| 2017/0281909 A1 | 10/2017 | Northrop et al. |
| 2017/0290599 A1 | 10/2017 | Youn et al. |
| 2017/0367707 A1 | 12/2017 | Divino |
| 2018/0049762 A1 | 2/2018 | Seip et al. |
| 2018/0084982 A1 | 3/2018 | Yamashita et al. |
| 2018/0116717 A1* | 5/2018 | Taff .................... A61B 18/1492 |
| 2018/0132876 A1 | 5/2018 | Zaidat |
| 2018/0133436 A1 | 5/2018 | Garrison et al. |
| 2018/0140314 A1 | 5/2018 | Goyal et al. |
| 2018/0140315 A1 | 5/2018 | Bowman et al. |
| 2018/0140354 A1 | 5/2018 | Lam et al. |
| 2018/0161514 A1 | 6/2018 | Rothenberg et al. |
| 2018/0161541 A1 | 6/2018 | Haldis et al. |
| 2018/0185614 A1 | 7/2018 | Garrison et al. |
| 2018/0200040 A1 | 7/2018 | Wasdyke et al. |
| 2018/0236221 A1 | 8/2018 | Opie et al. |
| 2018/0303595 A1 | 10/2018 | Opie et al. |
| 2018/0344970 A1 | 12/2018 | Kornowski et al. |
| 2019/0038438 A1 | 2/2019 | John et al. |
| 2019/0046119 A1 | 2/2019 | Oxley |
| 2019/0175199 A1 | 6/2019 | Girdhar et al. |
| 2019/0175200 A1 | 6/2019 | Girdhar et al. |
| 2019/0262069 A1 | 8/2019 | Taff et al. |
| 2019/0388097 A1 | 12/2019 | Girdhar et al. |
| 2019/0388107 A1 | 12/2019 | Girdhar et al. |
| 2019/0388111 A1 | 12/2019 | Nguyen et al. |
| 2019/0388112 A1 | 12/2019 | Nguyen et al. |
| 2020/0054392 A1 | 2/2020 | Whiteley et al. |
| 2020/0129742 A1 | 4/2020 | Cope et al. |
| 2020/0297367 A1 | 9/2020 | Girdhar et al. |
| 2020/0297410 A1 | 9/2020 | Nguyen et al. |
| 2020/0390455 A1 | 12/2020 | Nguyen et al. |
| 2020/0390456 A1 | 12/2020 | Nguyen et al. |
| 2020/0390457 A1 | 12/2020 | Nageswaran et al. |
| 2020/0390458 A1 | 12/2020 | Nguyen et al. |
| 2021/0068853 A1 | 3/2021 | Nguyen et al. |
| 2021/0137542 A1 | 5/2021 | Oxley et al. |
| 2021/0177427 A1 | 6/2021 | Nguyen et al. |
| 2021/0177442 A1 | 6/2021 | Girdhar et al. |
| 2021/0177446 A1 | 6/2021 | Girdhar et al. |
| 2021/0186540 A1 | 6/2021 | Taff et al. |
| 2021/0238764 A1 | 8/2021 | Tyvoll et al. |
| 2021/0267612 A1 | 9/2021 | Girdhar et al. |
| 2022/0022899 A1 | 1/2022 | Girdhar et al. |
| 2022/0125455 A1 | 4/2022 | Girdhar et al. |
| 2022/0202431 A1 | 6/2022 | Davidson et al. |
| 2022/0218372 A1 | 7/2022 | Nguyen et al. |
| 2022/0236569 A1 | 7/2022 | Yamazaki et al. |
| 2022/0387051 A1 | 12/2022 | Girdhar et al. |
| 2022/0387098 A1 | 12/2022 | Girdhar et al. |

FOREIGN PATENT DOCUMENTS

| | | | |
|---|---|---|---|
| CN | 104994799 A | | 10/2015 |
| CN | 107405160 A | | 11/2017 |
| CN | 104884681 B | | 5/2018 |
| EP | 1484025 A1 | | 12/2004 |
| EP | 2319575 B1 | | 11/2013 |
| EP | 2490764 B1 | | 9/2014 |
| EP | 2895645 A1 | | 7/2015 |
| EP | 2967605 A1 | | 1/2016 |
| EP | 3184067 A1 | | 6/2017 |
| JP | 10290805 A | | 11/1998 |
| JP | 2014004219 A | | 1/2014 |
| JP | 2018118132 A | | 8/2018 |
| KR | 20180102877 A | | 9/2018 |
| WO | 0035363 A1 | | 6/2000 |
| WO | 2009127037 A1 | | 10/2009 |
| WO | 2010061376 A1 | | 6/2010 |
| WO | 2014079148 A1 | | 5/2014 |
| WO | 2015141317 A1 | | 9/2015 |
| WO | 2016007388 A1 | | 1/2016 |
| WO | 2016141025 A1 | | 9/2016 |
| WO | 2016198947 A1 | | 12/2016 |
| WO | 2017192999 A1 | | 11/2017 |
| WO | 2018019829 A1 | | 2/2018 |
| WO | 2018033401 A1 | | 2/2018 |
| WO | 2018046408 A2 | | 3/2018 |
| WO | 2018127796 A1 | | 7/2018 |
| WO | 2018137029 A1 | | 8/2018 |
| WO | 2018137030 A1 | | 8/2018 |
| WO | 2018145212 A1 | | 8/2018 |
| WO | 2018156813 A1 | | 8/2018 |
| WO | 2018172891 A1 | | 9/2018 |
| WO | WO-2018172891 A1 * | 9/2018 | ......... A61B 18/1492 |
| WO | 2018187776 A1 | | 10/2018 |
| WO | 2019102307 A1 | | 5/2019 |
| WO | 2019246377 A2 | | 12/2019 |

OTHER PUBLICATIONS

Extended European Search Report dated Jul. 15, 2021; European Application No. 18888795.4; 6 pages.

International Search Report and Written Opinion dated Feb. 26, 2021; International Application No. PCT/US20/63200; 14 pages.

International Search Report and Written Opinion dated May 25, 2020, International Application No. PCT/US20/22463, 10 pages.

International Search Report and Written Opinion dated Nov. 3, 2020, International Application No. PCT/US20/70142, 18 pages.

"U.S. Appl. No. 15/838,214, filed Dec. 11, 2017".

"U.S. Appl. No. 15/838,230, filed Dec. 11, 2017".

Fort, Stephen , et al., "'Fused-Gold' vs. 'Bare' stainless steel NIRflex stents of the same geometric design in diseased native coronary arteries. Long-term results from the NIR TOP Study", Euro Interv 2007; 3:256-261.

* cited by examiner

ELECTRICALLY ENHANCED RETRIEVAL OF MATERIAL FROM VESSEL LUMENS

CROSS-REFERENCE TO RELATED APPLICATION(S)

The present application is a divisional of U.S. patent application Ser. No. 16/024,388, filed Jun. 29, 2018, which claims priority to U.S. Provisional Application No. 62/688,636, filed Jun. 22, 2018, each of which are incorporated by reference herein in their entirety.

TECHNICAL FIELD

The present technology relates generally to devices and methods for removing obstructions from body lumens. Some embodiments of the present technology relate to devices and methods for electrically enhanced removal of clot material from blood vessels.

BACKGROUND

Many medical procedures use medical device(s) to remove an obstruction (such as clot material) from a body lumen, vessel, or other organ. An inherent risk in such procedures is that mobilizing or otherwise disturbing the obstruction can potentially create further harm if the obstruction or a fragment thereof dislodges from the retrieval device. If all or a portion of the obstruction breaks free from the device and flows downstream, it is highly likely that the free material will become trapped in smaller and more tortuous anatomy. In many cases, the physician will no longer be able to use the same retrieval device to again remove the obstruction because the device may be too large and/or immobile to move the device to the site of the new obstruction.

Procedures for treating ischemic stroke by restoring flow within the cerebral vasculature are subject to the above concerns. The brain relies on its arteries and veins to supply oxygenated blood from the heart and lungs and to remove carbon dioxide and cellular waste from brain tissue. Blockages that interfere with this blood supply eventually cause the brain tissue to stop functioning. If the disruption in blood occurs for a sufficient amount of time, the continued lack of nutrients and oxygen causes irreversible cell death. Accordingly, it is desirable to provide immediate medical treatment of an ischemic stroke.

To access the cerebral vasculature, a physician typically advances a catheter from a remote part of the body (typically a leg) through the abdominal vasculature and into the cerebral region of the vasculature. Once within the cerebral vasculature, the physician deploys a device for retrieval of the obstruction causing the blockage. Concerns about dislodged obstructions or the migration of dislodged fragments increases the duration of the procedure at a time when restoration of blood flow is paramount. Furthermore, a physician might be unaware of one or more fragments that dislodge from the initial obstruction and cause blockage of smaller more distal vessels.

Many physicians currently perform thrombectomies (i.e. clot removal) with stents to resolve ischemic stroke. Typically, the physician deploys a stent into the clot in an attempt to push the clot to the side of the vessel and re-establish blood flow. Tissue plasminogen activator ("tPA") is often injected into the bloodstream through an intravenous line to break down a clot. However, it takes time for the tPA to reach the clot because the tPA must travel through the vasculature and only begins to break up the clot once it reaches the clot material. tPA is also often administered to supplement the effectiveness of the stent. Yet, if attempts at clot dissolution are ineffective or incomplete, the physician can attempt to remove the stent while it is expanded against or enmeshed within the clot. In doing so, the physician must effectively drag the clot through the vasculature, in a proximal direction, into a guide catheter located within vessels in the patient's neck (typically the carotid artery). While this procedure has been shown to be effective in the clinic and easy for the physician to perform, there remain some distinct disadvantages to using this approach.

For example, one disadvantage is that the stent may not sufficiently retain the clot as it pulls the clot to the catheter. In such a case, some or all of the clot might remain in the vasculature. Another risk is that, as the stent mobilizes the clot from the original blockage site, the clot might not adhere to the stent as the stent is withdrawn toward the catheter. This is a particular risk when passing through bifurcations and tortuous anatomy. Furthermore, blood flow can carry the clot (or fragments of the clot) into a branching vessel at a bifurcation. If the clot is successfully brought to the end of the guide catheter in the carotid artery, yet another risk is that the clot may be "stripped" or "sheared" from the stent as the stent enters the guide catheter.

In view of the above, there remains a need for improved devices and methods that can remove occlusions from body lumens and/or vessels.

SUMMARY

Mechanical thrombectomy (i.e., clot-grabbing and removal) has been effectively used for treatment of ischemic stroke. Although most clots can be retrieved in a single pass attempt, there are instances in which multiple attempts are needed to fully retrieve the clot and restore blood flow through the vessel. Additionally, there exist complications due to detachment of the clot from the interventional element during the retrieval process as the interventional element and clot traverse through tortuous intracranial vascular anatomy. For example, the detached clot or clot fragments can obstruct other arteries leading to secondary strokes. The failure modes that contribute to clot release during retrieval are: (a) boundary conditions at bifurcations; (b) changes in vessel diameter; and (c) vessel tortuosity, amongst others.

Certain blood components, such as platelets and coagulation proteins, display negative electrical charges. The treatment systems of the present technology provide an interventional element and a current generator configured to positively charge the interventional element during one or more stages of a thrombectomy procedure. For example, the current generator may apply a constant or pulsatile direct current (DC) to the interventional element. The positively charged interventional element attracts negatively charged blood components, thereby improving attachment of the thrombus to the interventional element and reducing the number of device passes or attempts necessary to fully retrieve the clot. In some aspects of the present technology, the treatment system includes a core member extending between the current generator and the interventional element. A delivery electrode may be integrated into the core member, and the treatment system further includes a return electrode that may be disposed at a number of different locations. For example, the return electrode can be a needle, a grounding pad, a conductive element carried by a one or more catheters of the treatment system, a guide wire, and/or any other suitable conductive element configured to complete an electrical circuit with the delivery electrode and the extracorporeally positioned current generator. When the interventional element is placed in the presence of blood (or any other electrolytic medium) and voltage is applied at the terminals of the current generator, current flows along the core member to the interventional element, through the blood, and to the return electrode, thereby positively charging at least a portion of the interventional element and adhering clot material thereto.

While applying a current to positively charge the interventional element can improve attachment of the thrombus to the interventional element, the inventors have discovered particularly effective waveforms and power delivery parameters for promoting thrombus attachment. It is important to provide sufficient current and power to enhance clot-adhesion without ablating tissue or generating new clots (i.e., the delivered power should not be significantly thrombogenic). The clot-adhesion effect appears to be driven by the peak current of the delivered electrical signal. Periodic (e.g., pulse-width modulated or pulsed direct current) waveforms can advantageously provide the desired peak current without delivering excessive total energy. In particular, non-square periodic waveforms can be especially effective in providing the desired peak current without delivering excessive total energy or electrical charge to the interventional element. In some embodiments, the overall charge delivered can be between about 30-1200 mC, the total energy delivered can be between about 120-24,000 mJ, and/or the peak current delivered can be between about 0.5-5 mA. In at least some embodiments, the duration of energy delivery can be between 30 seconds and 5 minutes, and in some embodiments no more than 2 minutes.

The treatment systems and methods of the present technology can further improve adhesion of the clot to the interventional element by varying features of the interventional element. For example, in some embodiments, some or all of the interventional element can be coated with one or more highly conductive materials, such as gold, to improve clot adhesion. In some aspects of the present technology, a working length of the interventional element may be coated with the conductive material while a non-working length of the interventional element may be coated with an insulative material.

Treatment systems and methods disclosed herein may also improve clot adhesion by modifying the environment at the treatment site. For example, the inventors have observed that blood flow at the treatment site reduces adhesion forces between clot material and the interventional element, even when the interventional element is positively charged. To address this loss of adhesion, the present technology provides systems and methods for arresting blood flow at the treatment site at least while supplying electrical energy to the treatment site. In addition, the present technology provides systems and methods for infusing certain fluids (such as saline and/or contrast) at the treatment site at least during energy delivery to improve conductivity at the treatment site for electrically enhanced clot adhesion.

Many of the treatment systems of the present technology include an aspiration catheter for applying negative pressure at the treatment site to secure the clot against a distal portion of the aspiration catheter (and/or other component of the treatment system). Aspiration also helps capture any newly formed clots to reduce the risk of downstream embolism. Suction may be applied before, during, and/or after supplying electrical energy to the interventional element. In some embodiments, a distal portion of the aspiration catheter may be configured for electrically enhanced clot adhesion such that clot engagement and retrieval may be performed without a separate interventional element. For example, in some aspects of the technology, the aspiration catheter may include a delivery electrode at its distal tip that is configured to be positively charged by the current generator. A return electrode may be disposed at a number of different locations, such as the aspiration catheter or another component of the treatment system (such as a guide catheter). Securement of the clot to the aspiration catheter via suction may be enhanced by the additional adhesion forces generated when the delivery electrode is positively charged.

The present technology is illustrated, for example, according to various aspects described below. Various examples of aspects of the present technology are described as numbered clauses (1, 2, 3, etc.) for convenience. These are provided as examples and do not limit the present technology. It is noted that any of the dependent clauses may be combined in any combination, and placed into a respective independent clause, e.g., clause (1, 23, 35, etc.). The other clauses can be presented in a similar manner.

Clause 1. A thrombectomy system, comprising:
a power source having a positive terminal;
an elongated member having a proximal end coupled to the power source and a distal end configured to be positioned within a blood vessel at or near a thrombus; and
an interventional element carried at the distal end of the elongated member and coupled to the positive terminal of the power source, wherein the interventional element includes a first metallic material and a second metallic material disposed on the first metallic material along at least a portion of the interventional element, and wherein the power source is configured to deliver a current to the interventional element to positively charge the interventional element and promote adhesion of the thrombus thereto.

Clause 2. The thrombectomy system of Clause 1, wherein the power source is configured to be extracorporeally positioned while the interventional element is positioned at or near the thrombus.

Clause 3. The thrombectomy system of Clause 1 or Clause 2, wherein an electrical conductivity of the second metallic material is greater than an electrical conductivity of the first metallic material.

Clause 4. The thrombectomy system of any one of Clauses 1 to 3, wherein the first metallic material is a superelastic alloy and the second metallic material is gold.

Clause 5. The thrombectomy system of any one of Clauses 1 to 4, wherein the first metallic material has a surface including an outward-facing portion that faces away from a central lumen of the interventional element, and wherein the second metallic material is disposed on the first metallic material only at the outward-facing portion and not at a remaining portion of the surface.

Clause 6. The thrombectomy system of any one of Clauses 1 to 5, wherein the interventional element comprises a working length portion and a non-working length portion, the working length portion being configured to interlock, capture, and/or engage a thrombus.

Clause 7. The thrombectomy system of Clause 6, wherein a distal terminus of the working length portion is proximal of a distal terminus of the interventional element.

Clause 8. The thrombectomy system of Clause 6 or Clause 7, wherein the working length portion is spaced apart from a distal terminus of the interventional element.

Clause 9. The thrombectomy system of any one of Clauses 6 to 8, wherein the non-working length portion is disposed between a distal end of the elongated member and a proximal end of the working length portion.

Clause 10. The thrombectomy system of any one of Clauses 6 to 9, wherein the second metallic material has a greater conductivity than the first metallic material and is disposed on the first metallic material only along the working length portion of the interventional element and not along the non-working length portion.

Clause 11. The thrombectomy system of any one of Clauses 6 to 10, wherein the second metallic material has a greater conductivity than the first metallic material and is disposed on the first metallic material only along the working length portion of the interventional element and not along (i) the non-working length portion and (ii) a distal-most region of the interventional element.

Clause 12. The thrombectomy system of any one of Clauses 6 to 11, wherein the non-working length portion is covered by a non-conductive and/or insulative material such that the non-working length portion is not in electrical contact with the surrounding media when the interventional element is deployed within a blood vessel.

Clause 13. The thrombectomy system of any one of Clauses 6 to 11, wherein the non-working length portion and a region of the interventional element distal of the working length portion are covered by a non-conductive and/or insulative material such that the non-working length portion and the region are not in electrical contact with the surrounding media when the interventional element is deployed within a blood vessel.

Clause 14. The thrombectomy system of any one of Clauses 6 to 11, wherein the second metallic material is selectively disposed on the first metallic material such that the delivered current is concentrated along the working length portion.

Clause 15. The thrombectomy system of any one of Clauses 1 to 14, wherein the power source is configured to deliver direct current to the interventional element.

Clause 16. The thrombectomy system of any one of Clauses 1 to 15, wherein the power source is configured to deliver pulsatile current to the interventional element.

Clause 17. The thrombectomy system of any one of Clauses 1 to 16, wherein the current is a constant current having an amplitude of between about 0.5 mA and about 5 mA.

Clause 18. The thrombectomy system of any one of Clauses 1 to 17, wherein the interventional element comprises a thrombectomy device.

Clause 19. The thrombectomy system of any one of Clauses 1 to 18, wherein the interventional element comprises a stent retriever.

Clause 20. The thrombectomy system of any one of Clauses 1 to 19, wherein the interventional element comprises a removal device.

Clause 21. The thrombectomy system of any one of Clauses 1 to 20, wherein the interventional element is a mesh.

Clause 22. The thrombectomy system of any one of Clauses 1 to 21, wherein the interventional element is a laser-cut stent.

Clause 23. A thrombectomy system, comprising:
a power source having a positive terminal;
a first catheter;
a second catheter configured to be slidably received through a lumen of the first catheter;
an elongated member configured to be slidably received through a lumen of the second catheter, the elongated member having a proximal end coupled to the power source and a distal end configured to be positioned within a blood vessel at or near a thrombus; and
an interventional element carried at the distal end of the elongated member and coupled to the positive terminal of the power source, wherein the interventional element includes a first metallic material and a second metallic material disposed on the first metallic material along at least a portion of the interventional element, and wherein the power source is configured to deliver a current to the interventional element to positively charge the interventional element and promote adhesion of the thrombus thereto.

Clause 24. The thrombectomy system of Clause 23, wherein the first catheter includes a flow arrest element configured to expand within the vessel lumen and at least partially arrest blood flow proximal of the thrombus.

Clause 25. The thrombectomy system Clause 23 or Clause 24, wherein the first catheter is a guide catheter and the second catheter is a microcatheter.

Clause 26. The thrombectomy system of any one of Clauses 23 to 25, wherein the thrombectomy system further includes a third catheter configured to be slidably received through the lumen of the first catheter.

Clause 27. The thrombectomy system of Clause 26, wherein the second catheter is configured to be slidably received within a lumen of the second catheter.

Clause 28. The thrombectomy system of Clause 26, wherein the first catheter is a guide catheter and the third catheter is a distal access catheter.

Clause 29. The thrombectomy system of Clause 26, wherein the first catheter is a guide catheter, the second catheter is a microcatheter, and the third catheter is a distal access catheter.

Clause 30. The thrombectomy system of Clause 26, wherein the third catheter is an aspiration catheter.

Clause 31. The thrombectomy system of Clause 26, wherein the first catheter is a balloon guide catheter and the third catheter is a distal access catheter.

Clause 32. The thrombectomy system Clause 26, wherein the first catheter is a guide catheter and the third catheter is a distal access catheter, wherein the distal access catheter includes a flow arrest element configured to expand within the vessel lumen and at least partially arrest blood flow proximal of the thrombus.

Clause 33. The thrombectomy system of Clause 32, wherein the distal access catheter is an aspiration catheter.

Clause 34. The thrombectomy system of any one of Clauses 26 to 33, wherein:
the first catheter includes a flow arrest element configured to expand within the vessel lumen and at least partially arrest blood flow proximal of the thrombus, and
the third catheter is an aspiration catheter configured to apply negative pressure at the treatment site.

Clause 35. A method, comprising:
intravascularly delivering an interventional element to a treatment site within a blood vessel, wherein the interventional element comprises a first metallic material and a second metallic material disposed on the first metallic material; and
while the interventional element is positioned at the treatment site, producing a positive charge along at least a portion of the interventional element via a power source coupled to the interventional element at an extracorporeal location.

Clause 36. The method of Clause 35, further comprising concentrating the positive charge along a working length of the interventional element, wherein a proximal end of the working length is distal of a proximal end of the interventional element and a distal end of the working length is proximal of a distal end of the interventional element.

Clause 37. The method of any one of Clauses 35 to 36, wherein producing a positive charge includes delivering a direct current to the interventional element from the power source.

Clause 38. The method of any one of Clauses 35 to 37, wherein producing a positive charge includes delivering a pulsatile current to the interventional element from the power source.

Clause 39. The method of any one of Clauses 35 to 38, wherein an electrical conductivity of the second metallic material is greater than an electrical conductivity of the first metallic material.

Clause 40. The method of any one of Clauses 35 to 39, wherein the second metallic material is gold.

Clause 41. The method of any one of Clauses 35 to 40, wherein producing a positive charge includes delivering a current to the interventional element, the current having an amplitude of between about 0.5 mA and about 5 mA.

Clause 42. The method of any one of Clauses 35 to 41, wherein producing a positive charge includes delivering a current to the interventional element, the current having an amplitude of about 2 mA.

Clause 43. The method of any one of Clauses 35 to 42, wherein the interventional element comprises a thrombectomy device.

Clause 44. The method of any one of Clauses 35 to 43, wherein the interventional element comprises a stent retriever.

Clause 45. The method of any one of Clauses 35 to 44, wherein the interventional element comprises a removal device.

Clause 46. The method of any one of Clauses 35 to 45, wherein the interventional element is a laser-cut stent or a mesh.

Clause 47. A method, comprising:
intravascularly delivering an interventional element to a treatment site within a blood vessel at or near a thrombus; and
while the interventional element is positioned at the treatment site and engaging the thrombus: (a) delivering a fluid to the treatment site, and (b) while at least some of the fluid is being delivered, applying a positive charge to the interventional element, thereby promoting adhesion of the thrombus to the interventional element.

Clause 48. The method of Clause 47, wherein an ion concentration of the fluid is greater than an ion concentration of blood.

Clause 49. The method of any one of Clauses 47 to 48, wherein the fluid is saline.

Clause 50. The method of any one of Clauses 47 to 48, wherein the fluid is contrast.

Clause 51. The method of any one of Clauses 47 to 50, wherein delivering the fluid to the treatment site increases an electrical conductivity at the treatment site.

Clause 52. The method of any one of Clauses 47 to 51, wherein delivering the fluid occurs while blood is flowing at the treatment site.

Clause 53. The method of any one of Clauses 47 to 51, wherein delivering the fluid occurs while blood flow is partially arrested at the treatment site.

Clause 54. The method of any one of Clauses 47 to 51, wherein delivering the fluid occurs while blood flow is completely arrested at the treatment site.

Clause 55. The method of any one of Clauses 47 to 54, further comprising expanding a flow arrest element within the blood vessel proximal of the treatment site before or while delivering the fluid.

Clause 56. The method of any one of Clauses 47 to 55, wherein the interventional element includes a first material and a second material disposed on the first material along at least a portion of the interventional element, wherein the second material is different than the first material.

Clause 57. The method of any one of Clauses 47 to 55, wherein the interventional element includes a first metallic material and a second metallic material disposed on the first metallic material along at least a portion of the interventional element, and wherein a conductivity of the second metallic material is greater than a conductivity of the first metallic material.

Clause 58. The method of Clause 57, wherein the second metallic material is gold.

Clause 59. The method of any one of Clauses 47 to 58, wherein applying a positive charge includes delivering an electric current to the interventional element from a power source positioned at an extracorporeal location.

Clause 60. The method of Clause 59, wherein the current is delivered while the interventional element is positioned at the treatment site.

Clause 61. The method of any one of Clauses 59 to 60, wherein the current has an amplitude of between about 0.5 mA and about 5 mA.

Clause 62. The method of any one of Clauses 59 to 61, wherein the current is a direct current.

Clause 63. The method of any one of Clauses 59 to 62, wherein the amplitude of the current remains generally constant.

Clause 64. The method of any one of Clauses 59 to 63, wherein the current is delivered for at least 30 seconds, at least 1 minute, or at least 2 minutes.

Clause 65. The method of any one of Clauses 47 to 64, wherein the interventional element comprises a thrombectomy device.

Clause 66. The method of any one of Clauses 47 to 65, wherein the interventional element comprises a stent retriever.

Clause 67. The method of any one of Clauses 47 to 66, wherein the interventional element comprises a removal device.

Clause 68. The method of any one of Clauses 47 to 67, wherein the interventional element is a mesh.

Clause 69. The method of any one of Clauses 47 to 68, wherein the interventional element is a laser-cut stent.

Clause 70. The method of any one of Clauses 47 to 69, wherein the fluid is delivered through a distal access catheter.

Clause 71. The method of any one of Clauses 47 to 70, wherein the fluid is a liquid.

Clause 72. A method, comprising:
intravascularly delivering thrombectomy device to a treatment site within a blood vessel at or near a thrombus;
positioning a catheter at the treatment site such that a distal end of the catheter is proximal of the thrombus; and
while the thrombectomy device is positioned at the treatment site and engaging the thrombus: (a) delivering a fluid through the catheter to the treatment site, wherein delivering the fluid increases an electrical conductivity at the treatment site; and (b) while at least some of the fluid is being delivered, delivering current to the thrombectomy device, thereby promoting adhesion of the thrombus to the thrombectomy device.

Clause 73. The method of Clause 72, wherein an ion concentration of the fluid is greater than an ion concentration of blood.

Clause 74. The method of any one of Clauses 72 to 73, wherein the fluid is saline.

Clause 75. The method of any one of Clauses 72 to 73, wherein the fluid is contrast.

Clause 76. The method of any one of Clauses 72 to 74, wherein delivering the fluid occurs while blood is flowing at the treatment site.

Clause 77. The method of any one of Clauses 72 to 74, wherein delivering the fluid occurs while blood flow is partially arrested at the treatment site.

Clause 78. The method of any one of Clauses 72 to 74, wherein delivering the fluid occurs while blood flow is completely arrested at the treatment site.

Clause 79. The method of any one of Clauses 72 to 78, wherein delivering current to the thrombectomy device positively charges the thrombectomy device.

Clause 80. The method of any one of Clauses 72 to 79, wherein the thrombectomy device comprises a braid.

Clause 81. The method of any one of Clauses 72 to 80, wherein the thrombectomy device comprises a stent retriever.

Clause 82. The method of any one of Clauses 72 to 81, wherein the thrombectomy device comprises a removal device.

Clause 83. The method of any one of Clauses 72 to 82, wherein the thrombectomy device is a mesh.

Clause 84. The method of any one of Clauses 72 to 83, wherein the thrombectomy device is a laser-cut stent.

Clause 85. A thrombectomy system, comprising:
a catheter having a distal portion configured to be positioned adjacent to a thrombus in a blood vessel;
an electrode disposed at the distal portion of the catheter, the electrode configured to be electrically coupled to an extracorporeal power supply; and
an interventional element configured to be delivered through a lumen of the catheter, the interventional element configured to be electrically coupled to the extracorporeal power supply.

Clause 86. The system of Clause 85, wherein the electrode is in electrical communication with a conductive lead extending proximally along the catheter.

Clause 87. The system of Clause 86, wherein the conductive lead is disposed within a wall of the catheter.

Clause 88. The system of Clause 86, wherein the conductive lead is disposed along an external surface of the catheter.

Clause 89. The system of any one of Clauses 85 to 88, wherein the electrode comprises a conductive band extending at least partially circumferentially around the distal portion of the catheter.

Clause 90. The system of Clause 89, wherein the conductive band is disposed on an inner surface of the catheter.

Clause 91. The system of Clause 89, wherein the conductive band is disposed on an outer surface of the catheter.

Clause 92. The system of any one of Clauses 85 to 91, wherein the electrode comprises a stent engaged with an inner surface of the catheter.

Clause 93. The system of any one of Clauses 85 to 92, wherein the catheter comprises an aspiration catheter.

Clause 94. The system of any one of Clauses 85 to 93, wherein the catheter comprises a distal access catheter.

Clause 95. The system of any one of Clauses 85 to 93, wherein the catheter comprises a guide catheter.

Clause 96. The system of any one of Clauses 85 to 93, wherein the catheter comprises a balloon guide catheter.

Clause 97. The system of any one of Clauses 85 to 96, wherein the catheter is a first catheter and the system further comprises a second catheter, wherein the first catheter is configured to be slidably disposed within a lumen of the second catheter.

Clause 98. The system of any one of Clauses 85 to 96, wherein the catheter is a first catheter and the system further comprises a second catheter, wherein the second catheter is configured to be slidably disposed within a lumen of the first catheter.

Clause 99. The system of any one of Clauses 85 to 98, wherein the catheter is a microcatheter.

Clause 100. The system of any one of Clauses 85 to 96, wherein the catheter is a first catheter and the system further comprises a second catheter and a third catheter, wherein the first catheter is configured to be slidably disposed within a lumen of the second catheter, and the second catheter is configured to be slidably disposed within a lumen of the third catheter.

Clause 101. The system of any one of Clauses 85 to 100, wherein the electrode comprises a conductive band extending at least partially circumferentially around the distal portion of the catheter.

Clause 102. The system of Clause 101, wherein the conductive band is disposed on an inner surface of the catheter.

Clause 103. The system of Clause 101, wherein the conductive band is disposed on an outer surface of the catheter.

Clause 104. The system of any one of Clauses 85 to 103, further comprising a suction source configured to supply negative pressure through the catheter to aspirate a region adjacent to the distal portion of the catheter.

Clause 105. The system of any one of Clauses 85 to 104, wherein the catheter is an aspiration catheter having a proximal portion configured to be fluidically coupled to a suction source.

Clause 106. The system of any one of Clauses 85 to 105, further comprising a power supply having positive and negative terminals, the electrode being coupled to the negative terminal and the interventional element being coupled to the positive terminal.

Clause 107. The system of any one of Clauses 85 to 106, wherein, when the interventional element and the distal portion of the catheter are in the presence of an electrolytic medium and voltage is supplied to the first and second electrical terminals, current flows from the interventional element to the electrode.

Clause 108. The system of any one of Clauses 85 to 107, wherein a proximal end of the interventional element is coupled to a distal end of a core member, the core member extending proximally through the catheter.

Clause 109. The system of Clause 108, wherein the core member comprises an electrically conductive wire extending along its length.

Clause 110. The system of Clause 109, wherein the core member comprises an insulative coating surrounding the wire along at least a portion of its length.

Clause 111. The system of any one of Clauses 85 to 110, wherein the interventional element is electrically conductive.

Clause 112. The system of any one of Clauses 85 to 111, wherein the interventional element comprises a thrombectomy device.

Clause 113. The system of any one of Clauses 85 to 112, wherein the interventional element comprises a stent retriever.

Clause 114. The system of any one of Clauses 85 to 113, wherein the interventional element comprises a removal device.

Clause 115. The system of any one of Clauses 85 to 114, wherein the interventional element comprises a catheter.

Clause 116. The system of any one of Clauses 85 to 115, wherein a portion of the interventional element is coated with a conductive material.

Clause 117. The system of Clause 116, wherein the conductive material comprises gold.

Clause 118. The system of any one of Clauses 85 to 117, wherein a portion of the interventional element is coated with a non-conductive material.

Clause 119. The system of Clause 118, wherein the non-conductive material comprises parylene.

Clause 120. A medical device delivery system, comprising:
- a medical device coupled to a distal end of an elongate shaft, the shaft configured to be electrically coupled to a first terminal of a power supply; and
- an elongate tubular member configured to receive the shaft therethrough, the tubular member having an electrode disposed at a distal portion thereof and a conductive lead electrically coupled to the electrode, the conductive lead extending along a length of the tubular member and configured to be electrically coupled to a second terminal of the power supply.

Clause 121. The system of Clause 120, wherein the shaft and the conductive lead are configured to be coupled to first and second terminals, respectively, of an extracorporeal power supply.

Clause 122. The system of any one of Clauses 120 to 121, wherein the shaft comprises a conductive element in electrical communication with the medical device Clause 123. The system of any one of Clauses 120 to 122, wherein the medical device is electrically conductive.

Clause 124. The system of any one of Clauses 120 to 123, wherein the conductive lead is disposed within a wall of the tubular member.

Clause 125. The system of any one of Clauses 120 to 123, wherein the conductive lead is disposed along an external surface of the tubular member.

Clause 126. The system of any one of Clauses 120 to 125, wherein the electrode comprises a conductive band extending at least partially circumferentially around the distal portion of the tubular member.

Clause 127. The system of Clause 126, wherein the conductive band is disposed on an inner surface of the tubular member.

Clause 128. The system of Clause 126, wherein the conductive band is disposed on an outer surface of the tubular member.

Clause 129. The system of any one of Clauses 120 to 128, wherein the electrode comprises a stent engaged with an inner surface of the tubular member.

Clause 130. The system of any one of Clauses 120 to 129, wherein the tubular member comprises an aspiration catheter.

Clause 131. The system of any one of Clauses 120 to 129, wherein the tubular member comprises a guide catheter.

Clause 132. The system of any one of Clauses 120 to 131, further comprising a suction source configured to supply negative pressure through the tubular member to aspirate a region adjacent to a distal portion of the tubular member.

Clause 133. The system of any one of Clauses 120 to 132, wherein the tubular member is an aspiration catheter having a proximal portion configured to be fluidically coupled to a suction source.

Clause 134. The system of any one of Clauses 120 to 133, further comprising a power supply having positive and negative terminals, the electrode being coupled to the negative terminal and the shaft being coupled to the positive terminal.

Clause 135. The system of Clause 134, wherein, when the medical device and the distal portion of the tubular member are in the presence of an electrolytic medium and voltage is supplied to the positive and negative terminals, current flows from the medical device the electrode.

Clause 136. The system of any one of Clauses 120 to 135, wherein the shaft comprises an electrically conductive wire extending along its length.

Clause 137. The system of Clause 136, wherein the shaft comprises an insulative coating surrounding the wire along at least a portion of its length.

Clause 138. The system of any one of Clauses 120 to 137, wherein the medical device comprises a thrombectomy device.

Clause 139. The system of any one of Clauses 120 to 138, wherein the medical device comprises a stent retriever.

Clause 140. The system of any one of Clauses 120 to 139, wherein the medical device comprises a removal device.

Clause 141. The system of any one of Clauses 120 to 140, wherein the medical device comprises a catheter.

Clause 142. The system of any one of Clauses 120 to 141, wherein a portion of the medical device is coated with a conductive material.

Clause 143. The system of Clause 142, wherein the conductive material comprises gold.

Clause 144. The system of any one of Clauses 120 to 143, wherein a portion of the medical device is coated with a non-conductive material.

Clause 145. The system of Clause 144, wherein the non-conductive material comprises parylene.

Clause 146. A method, comprising:
- disposing a distal portion of a catheter adjacent to a treatment site in the body, the catheter comprising an electrode disposed in the distal portion and coupled to a first electrical terminal of a power supply;
- advancing an interventional element through the catheter to the treatment site, the interventional element coupled to a second electrical terminal of a power supply; and
- supplying electric current to the second electrical terminal.

Clause 147. The method of Clause 146, further comprising ceasing the supplying of electric current to the second electrical terminal after a first time period.

Clause 148. The method of Clause 147, further comprising, after ceasing the supplying of electric current, proximally retracting the core member with respect to the catheter.

Clause 149. The method of any one of Clauses 147 to 148, wherein the first time period is less than about 5 minutes.

Clause 150. The method of any one of Clauses 147 to 149, wherein the first time period is less than about 2 minutes.

Clause 151. The method of any one of Clauses 146 to 150, wherein the electrode is coupled to the first electrical terminal via a conductive lead extending proximally along the catheter.

Clause 152. The method of Clause 151, wherein the conductive lead is disposed within a wall of the catheter.

Clause 153. The method of Clause 151, wherein the conductive lead is disposed along an external surface of the catheter.

Clause 154. The method of any one of Clauses 146 to 153, wherein the electrode comprises a conductive band extending at least partially circumferentially around the distal portion of the catheter.

Clause 155. The method of Clause 154, wherein the conductive band is disposed on an inner surface of the catheter.

Clause 156. The method of Clause 154, wherein the conductive band is disposed on an outer surface of the catheter.

Clause 157. The method of any one of Clauses 146 to 156, wherein the electrode comprises a stent engaged with an inner surface of the catheter.

Clause 158. The method of any one of Clauses 146 to 157, further comprising supplying negative pressure through the catheter to aspirate a region adjacent to the treatment site.

Clause 159. The method of any one of Clauses 146 to 158, wherein the treatment site in the body is proximate to or adjacent to a thrombus in a blood vessel.

Clause 160. The method of any one of Clauses 146 to 159, further comprising, after advancing the interventional element through the catheter, expanding the interventional element adjacent to a thrombus in a blood vessel.

Clause 161. The method of any one of Clauses 146 to 160, wherein the interventional element comprises a thrombectomy device.

Clause 162. The method of any one of Clauses 146 to 161, wherein the interventional element comprises a stent retriever.

Clause 163. The method of any one of Clauses 146 to 162, wherein the interventional element comprises a removal device.

Clause 164. The method of any one of Clauses 146 to 163, wherein the interventional element is coupled to the second electrical terminal of the power supply via a conductive pushwire.

Clause 165. The method of any one of Clauses 146 to 164, further comprising:
  arresting blood flow at the treatment site; and
  after arresting the blood flow, supplying the electric current to the second electrical terminal.

Clause 166. The method of Clause 165, further comprising:
  ceasing the supplying of electric current to the second electrical terminal after a first time period; and
  after ceasing the supplying of electric current, restoring blood flow at the treatment site.

Clause 167. The method of any one of Clauses 165 to 166, wherein arresting the blood flow comprises expanding a balloon of a balloon-guide catheter at a position proximal to the treatment site.

Clause 168. An aspiration device, comprising:
  an aspiration catheter having a distal end configured to be positioned adjacent to a thrombus in a blood vessel and a proximal end configured to be fluidically coupled to a suction source;
  an electrode disposed at a distal portion of the aspiration catheter; and
  a conductive lead coupled to the electrode and extending along a length of the catheter, the lead configured to be coupled to a positive terminal of an extracorporeal power supply.

Clause 169. The device of Clause 168, wherein the electrode comprises a conductive band extending at least partially circumferentially around the distal portion of the catheter.

Clause 170. The device of Clause 169, wherein the conductive band is disposed on an inner surface of the catheter.

Clause 171. The device of any one of Clauses 168 to 170, wherein the conductive lead comprises a wire disposed within a wall of the catheter.

Clause 172. The device of any one of Clauses 168 to 170, wherein the conductive lead comprises a wire disposed around an external surface of the catheter.

Clause 173. The device of any one of Clauses 168 to 172, further comprising:
  a second electrode; and
  a second conductive lead coupled to the second electrode, the second conductive lead configured to be coupled to a negative terminal of the extracorporeal power supply.

Clause 174. The device of Clause 173, wherein the second electrode comprises a conductive band disposed at the distal portion of the catheter, and wherein the second conductive lead comprises a wire disposed within a wall of the catheter.

Clause 175. The device of Clause 173, wherein the second electrode comprises a conductive band disposed at the distal portion of the catheter, and wherein the second conductive lead comprises a wire disposed around an external surface of the catheter.

Clause 176. The device of Clause 173, wherein the second electrode comprises a flow-arrest element coupled to the distal portion of the catheter.

Clause 177. The device of Clause 173, wherein the second electrode is physically separate from the catheter.

Clause 178. The device of Clause 177, wherein the second electrode comprises a needle.

Clause 179. The device of Clause 177, wherein the second electrode comprises a grounding pad.

Clause 180. The device of any one of Clauses 168 to 179, further comprising a suction source configured to supply negative pressure through the catheter to aspirate a region adjacent to the distal portion of the catheter.

Clause 181. The device of any one of Clauses 168 to 180, further comprising a power supply having positive and negative terminals, the conductive lead being coupled to the positive terminal and a return electrode being coupled to the negative terminal.

Clause 182. A method, comprising:
  disposing a distal portion of a catheter adjacent to a treatment site in the body, the catheter comprising a first electrode disposed in the distal portion and coupled to a first electrical terminal of a power supply;
  supplying electric current to the first electrical terminal; and
  supplying negative pressure through the catheter to aspirate a region adjacent to the treatment site.

Clause 183. The method of Clause 182, further comprising disposing a second electrode at a position spaced apart from the first electrode, the second electrode coupled to a second electrical terminal of the power supply.

Clause 184. The method of Clause 183, wherein the first electrical terminal is positive, and wherein the second electrical terminal is negative.

Clause 185. The method of any one of Clauses 183 to 184, wherein the second electrode comprises a needle.

Clause 186. The method of any one of Clauses 183 to 184, wherein the second electrode comprises a grounding pad.

Clause 187. The method of any one of Clauses 183 to 184, wherein the second electrode comprises a conductive element disposed in the distal portion of the catheter.

Clause 188. The method of any one of Clauses 182 to 187, further comprising supplying the electric current to the first electrical terminal while supplying the negative pressure through the catheter.

Clause 189. The method of any one of Clauses 182 to 188, further comprising ceasing the supplying of electric current to the first electrical terminal after a first time period.

Clause 190. The method of Clause 189, wherein the first time period is less than about 5 minutes.

Clause 191. The method of Clause 189, wherein the first time period is less than about 2 minutes.

Clause 192. The method of any one of Clauses 182 to 191, wherein the first electrode is coupled to the first electrical terminal via a conductive lead extending proximally along the catheter.

Clause 193. The method of Clause 192, wherein the conductive lead is disposed within a wall of the catheter.

Clause 194. The method of Clause 192, wherein the conductive lead is disposed along an external surface of the catheter.

Clause 195. The method of Clause 182 to 194, wherein the first electrode comprises a conductive band extending at least partially circumferentially around the distal portion of the catheter.

Clause 196. The method of Clause 195, wherein the conductive band is disposed on an inner surface of the catheter.

Clause 197. The method of Clause 195, wherein the conductive band is disposed on an outer surface of the catheter.

Clause 198. The method of any one of Clauses 182 to 197, wherein the first electrode comprises a stent engaged with an inner surface of the catheter.

Clause 199. The method of any one of Clauses 182 to 198, wherein the treatment site in the body is proximate to or adjacent to a thrombus in a blood vessel.

Additional features and advantages of the present technology are described below, and in part will be apparent from the description, or may be learned by practice of the present technology. The advantages of the present technology will be realized and attained by the structure particularly pointed out in the written description and claims hereof as well as the appended drawings.

BRIEF DESCRIPTION OF THE DRAWINGS

Many aspects of the present technology can be better understood with reference to the following drawings. The components in the drawings are not necessarily to scale. Instead, emphasis is placed on illustrating clearly the principles of the present disclosure.

DETAILED DESCRIPTION

The present technology provides devices, systems, and methods for removing clot material from a blood vessel lumen. Although many of the embodiments are described below with respect to devices, systems, and methods for treating a cerebral or intracranial embolism, other applications and other embodiments in addition to those described herein are within the scope of the technology. For example, the treatment systems and methods of the present technology may be used to remove emboli from body lumens other than blood vessels (e.g., the digestive tract, etc.) and/or may be used to remove emboli from blood vessels outside of the brain (e.g., pulmonary, abdominal, cervical, or thoracic blood vessels, or peripheral blood vessels including those within the legs or arms, etc.). In addition, the treatment systems and methods of the present technology may be used to remove luminal obstructions other than clot material (e.g., plaque, resected tissue, foreign material, etc.).

I. Select Embodiments of Electrically Enhanced Treatment Systems

Figure 1A:
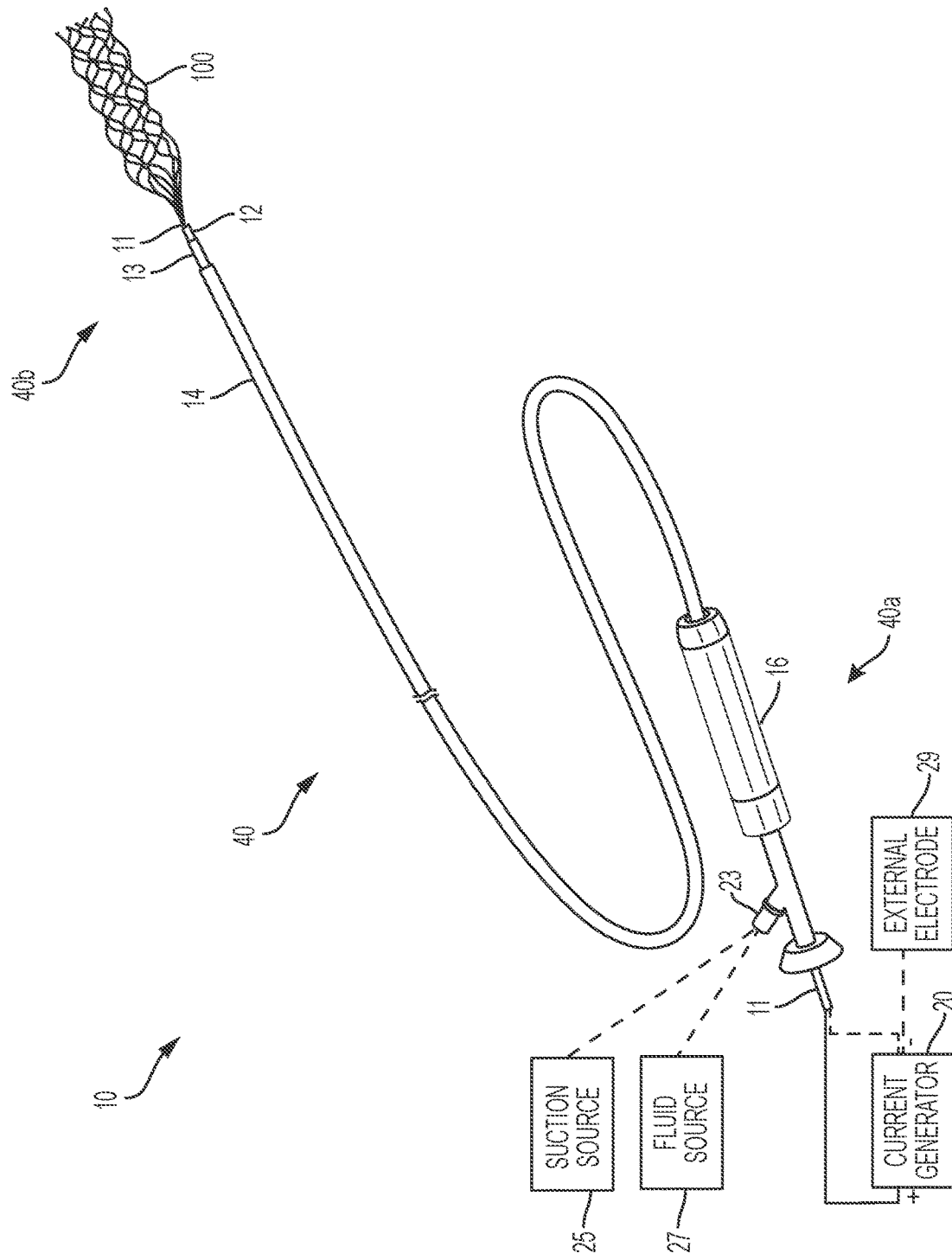
FIG. 1A shows a perspective view of an electrically enhanced treatment system for retrieving material from a body lumen, in accordance with one or more embodiments of the present technology.

FIG. 1A illustrates a view of an electrically enhanced treatment system 10 according to one or more embodiments of the present technology. As shown in FIG. 1A, the treatment system 10 can include a current generator 20 and a treatment device 40 having a proximal portion 40a configured to be coupled to the current generator 20 and a distal portion 40b configured to be intravascularly positioned within a blood vessel (such as an intracranial blood vessel) at a treatment site at or proximate a thrombus. The treatment device 40 includes an interventional element 100 at the distal portion 10b, a handle 16 at the proximal portion 10a, and a plurality of elongated shafts or members extending therebetween. For example, in some embodiments, such as that shown in FIG. 1A, the treatment device 40 includes a first catheter 14 (such as a balloon guide catheter), a second catheter 13 (such as a distal access catheter or aspiration catheter) configured to be slidably disposed within a lumen of the first catheter 14, a third catheter 12 (such as a microcatheter) configured to be slidably disposed within a lumen of the second catheter 13, and a core member 11 configured to be slidably disposed within a lumen of the third catheter 12. In some embodiments, the treatment device 40 does not include the second catheter 13. The first catheter 14 can be coupled to the handle 16, which provides proximal access to the core member 11 that engages the interventional element 100 at a distal end thereof. The current generator 20 may be coupled to a proximal portion of one or more of the core member 11, the third catheter 12, the second catheter 13, and/or the first catheter 14 to provide an electrically charged environment at the distal portion 40b of the treatment device 40, as described in more detail below.

In some embodiments, the treatment system 10 includes a suction source 25 (e.g., a syringe, a pump, etc.) configured to be fluidly coupled (e.g., via a connector 23) to a proximal portion of one or more of the first catheter 14, the second catheter 13, and/or the third catheter 12 to apply negative pressure therethrough. In some embodiments, the treatment system 10 includes a fluid source 27 (e.g., a fluid reservoir, a syringe, pump, etc.) configured to be fluidly coupled (e.g., via the connector 23) to a proximal portion of one or more of the first catheter 14, the second catheter 13, and/or the third catheter 12 to supply fluid (e.g., saline, contrast agents, a drug such as a thrombolytic agent, etc.) to the treatment site.

Figure 1B:
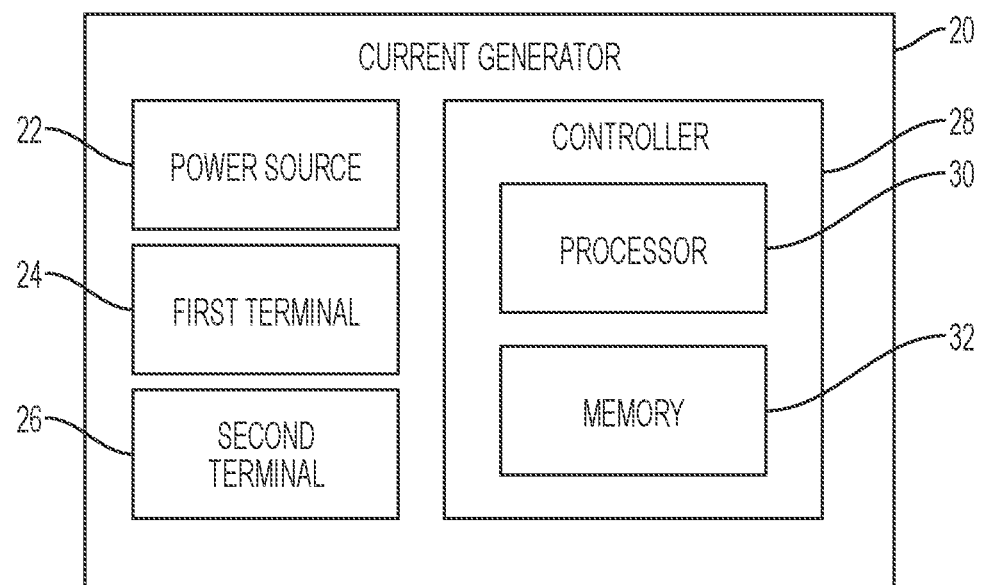
FIGS. 1B and 1C are schematic views of different embodiments of the current generator illustrated in FIG. 1A.
Figure 1C:
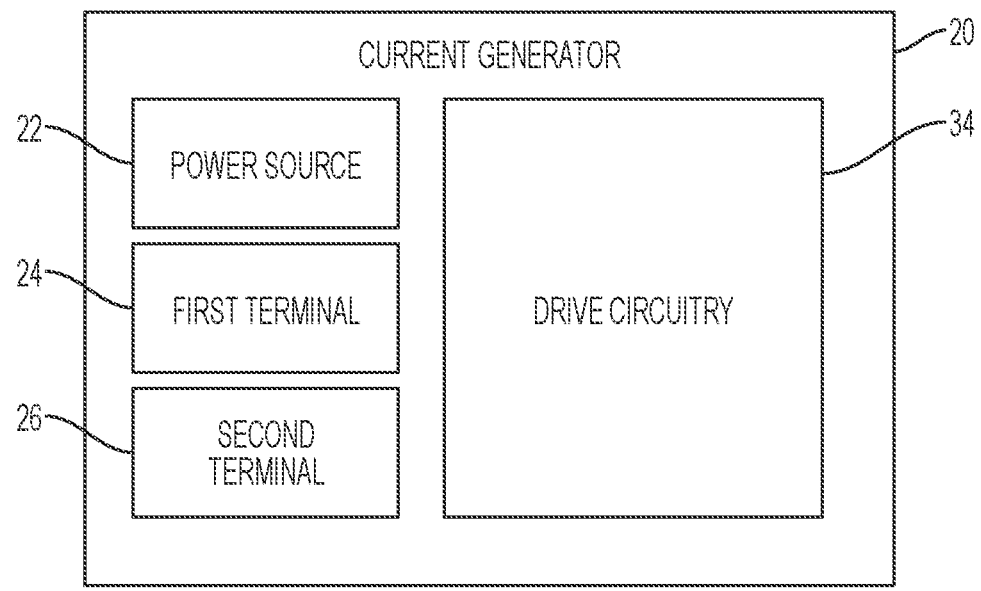

According to some embodiments, the current generator 20 can include an electrical generator configured to output medically useful electric current. FIGS. 1B and 1C are schematic views of different embodiments of the current generator 20. With reference to FIG. 1B, the current generator 20 can include a power source 22, a first terminal 24, a second terminal 26, and a controller 28. The controller 28 includes a processor 30 coupled to a memory 32 that stores instructions (e.g., in the form of software, code or program instructions executable by the processor or controller) for causing the power source 22 to deliver electric current according to certain parameters provided by the software, code, etc. The power source 22 of the current generator 20 may include a direct current power supply, an alternating current power supply, and/or a power supply switchable between a direct current and an alternating current. The current generator 20 can include a suitable controller that can be used to control various parameters of the energy output by the power source or generator, such as intensity, amplitude, duration, frequency, duty cycle, and polarity. For example, the current generator 20 can provide a voltage of about 2 volts to about 28 volts and a current of about 0.5 mA to about 20 mA.

FIG. 1C illustrates another embodiment of the current generator 20, in which the controller 28 of FIG. 1B is replaced with drive circuitry 34. In this embodiment, the current generator 20 can include hardwired circuit elements to provide the desired waveform delivery rather than a software-based generator of FIG. 1B. The drive circuitry 34 can include, for example, analog circuit elements (e.g., resistors, diodes, switches, etc.) that are configured to cause the power source 22 to deliver electric current via the first and second terminals 24, 26 according to the desired parameters. For example, the drive circuitry 34 can be configured to cause the power source 22 to deliver periodic waveforms via the first and second terminals 24, 26.

As noted above, the current generator 20 may be coupled to a proximal portion of the core member 11, and/or a proximal portion of the third catheter 12, the second catheter 13, and/or first catheter 14 to provide an electric current to the interventional element 100. For example, in some embodiments, both terminals of the current generator 20 are coupled to the core member 11 such that the core member 11 functions as both a delivery electrode or conductive path (i.e., transmitting current from the current generator 20 to the treatment site) and a return electrode or conductive path (i.e., transmitting current from the treatment site to the current generator 20) (described in greater detail below with reference to FIG. 2B). In other embodiments, the return electrode can be separate from the core member 11. For example, the return electrode can be carried by one or more of the third catheter 12, the second catheter 13, and/or first catheter 14. In some embodiments, the return electrode can be provided via one or more external electrodes 29 (FIG. 1A), such as a needle puncturing the patient or a grounding pad applied to the patient's skin. In some embodiments, the return electrode can be an insulated guide wire having an exposed, electrically conductive portion at its distal end.

Figure 2A:
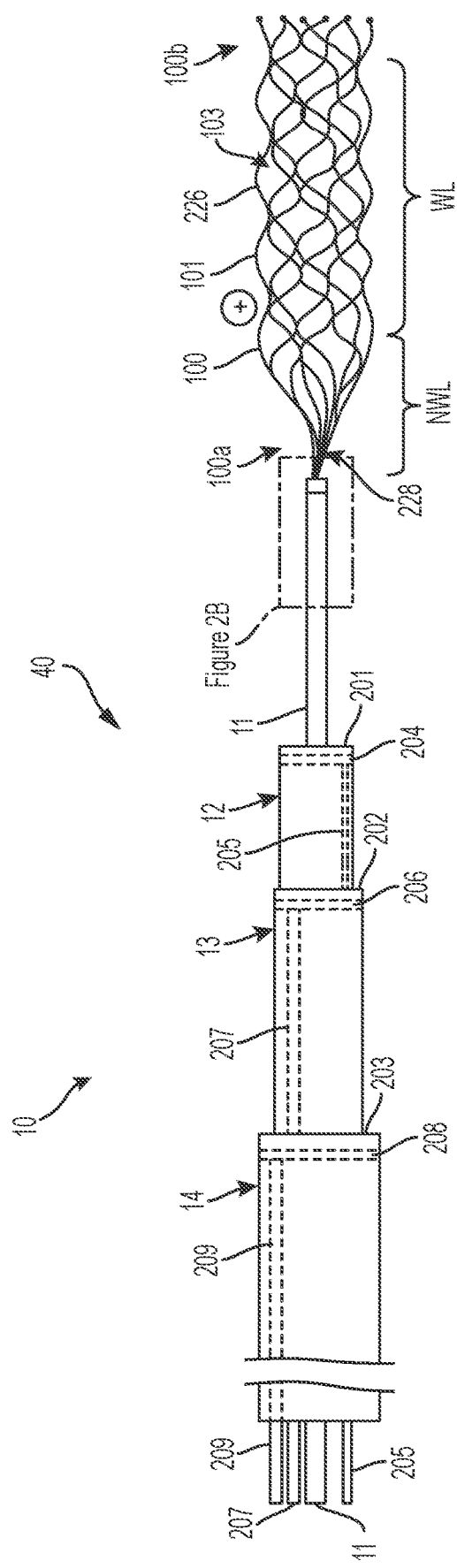
FIG. 2A is a side schematic view of a portion of the treatment system of FIG. 1A.

FIG. 2A is a side schematic view of a portion of the treatment device 40 shown in FIG. 1A. The system 10 can include can include multiple (e.g., two or more), distinct conductive paths or channels for passing electrical current along the system 10. The interventional element 100 can serve as one electrode (e.g., the delivery electrode) in electrical communication with a conductive path integrated into the core member 11. Another of the conductive paths of the system 10 can be in electrical communication with another electrode (e.g., a return electrode). The various embodiments of the core member 11 can be sized for insertion into a bodily lumen, such as a blood vessel, and can be configured to push and pull a device such as the interventional element 100 along the bodily lumen.

Figure 2B:
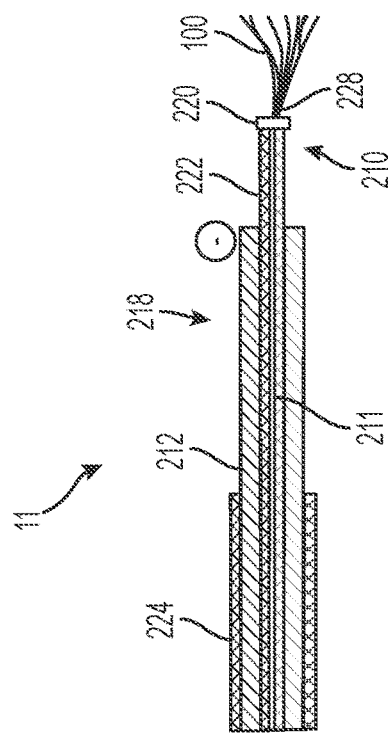
FIG. 2B is a side schematic cross-sectional view of a portion of the treatment system shown in FIG. 2A.

As noted above, the interventional element 100 can serve as the delivery electrode and be electrically coupled to a positive terminal of the current generator 20 (FIG. 1A). As shown in FIG. 2B, in some embodiments, the core member 11 can include an elongate conductive shaft 211 (e.g., a pushwire) extending along the length of the core member 11. The shaft can be in electrical communication with the current generator 20 (FIG. 1A) at its proximal end and the interventional element 100 at its distal end. The shaft can be insulated along at least a portion of its length, with exposed portions permitting electrical communication with the current generator 20 and the interventional element 100.

The return electrode(s) can assume a variety of configurations in different embodiments. For example, in some embodiments, the return electrode is an external electrode 29 (FIG. 1A), such as a needle or grounding pad that is applied to a patient's skin. The needle or grounding pad can be coupled via one or more leads to the current generator 20 to complete the electrical circuit. In some embodiments, the return electrode is carried by a surrounding catheter (e.g., third catheter 12, second catheter 13, and/or first catheter 14), as described in more detail below.

According to some embodiments, for example as shown in FIG. 2A, the catheters 12, 13, and 14 can each be formed as a generally tubular member extending along and about a central axis and terminating in a respective distal end 201, 202, and 203. According to some embodiments, the third catheter 12 is generally constructed to track over a conventional guidewire in the cervical anatomy and into the cerebral vessels associated with the brain and may also be chosen according to several standard designs that are generally available. Accordingly, the third catheter 12 can have a length that is at least 125 cm long, and more particularly may be between about 125 cm and about 175 cm long. Other designs and dimensions are contemplated.

The second catheter 13 can be sized and configured to be slidably receive the third catheter 12 therethrough. As noted above, the second catheter 13 can be coupled at a proximal portion to a suction source 25 (FIG. 1A) such as a pump or syringe in order to supply negative pressure to a treatment site. The first catheter 14 can be sized and configured to slidably receive both the second catheter 13 and the third catheter 12 therethrough. In some embodiments, the first catheter 14 is a balloon-guide catheter having an inflatable balloon or other expandable member that can be used to anchor the first catheter 14 with respect to a surrounding vessel. As described in more detail below with respect to FIGS. 4A-4G, in operation the first catheter 14 can first be advanced through a vessel and then a balloon can be expanded to anchor the first catheter 14 in place and/or arrest blood flow from areas proximal of the balloon. Next, the second catheter 13 can be advanced through the first catheter 14 until its distal end 202 extends distally beyond the distal end 203 of the first catheter 14. The second catheter 13 can be positioned such that its distal end 202 is adjacent a treatment site (e.g., a site of a blood clot within the vessel). The third catheter 12 may then be advanced through the second catheter 13 until its distal end 201 extends distally beyond the distal end 202 of the second catheter 13. The interventional element 100 may then be advanced through the third catheter 12 for delivery to the treatment site.

According to some embodiments, the bodies of the catheters 12, 13, and 14 can be made from various thermoplastics, e.g., polytetrafluoroethylene (PTFE or TEFLON®), fluorinated ethylene propylene (FEP), high-density polyethylene (HDPE), polyether ether ketone (PEEK), etc., which can optionally be lined on the inner surface of the catheters or an adjacent surface with a hydrophilic material such as polyvinylpyrrolidone (PVP) or some other plastic coating. Additionally, either surface can be coated with various combinations of different materials, depending upon the desired results.

According to some embodiments, an electrode 204 is provided at a distal end region of the third catheter 12. The electrode 204 can form an annular ring that extends entirely circumferentially about the central axis of the third catheter 12. Alternatively or in combination, the electrode 204 can extend less than entirely circumferentially around the third catheter 12. For example, the electrode 204 may be entirely disposed on one radial side of the central axis. By further example, the electrode 204 may provide a plurality of discrete, noncontiguous electrode sections about the central axis. Such sections of the electrode 204 can be in electrical communication with a common conductive path so as to function collectively as a single electrode, or with multiple separate such paths to allow the sections to function independently if desired. The electrode 201 can be a band, a wire, or a coil embedded in the wall of the third catheter 12. According to some embodiments, the electrode 204 can be longitudinally separated from the distal end 201 of the third catheter 12 by a non-conductive portion of the third catheter 12. Alternatively, a distal portion of the electrode 204 can extend to the distal end 201 of the third catheter 12, such that the electrode 204 forms a portion of the distal end 201. According to some embodiments, an inner surface of the electrode 204 can be flush with an inner surface of the third catheter 12. Alternatively or in combination, the inner surface of the electrode 204 can extend more radially inwardly relative to the inner surface of the third catheter 12 (e.g., providing a "step"). Alternatively or in combination, the inner surface of the electrode 204 can extend less radially inwardly relative to the inner surface of the third catheter 12 (e.g., be recessed into the body). According to some embodiments, the electrode 201 can be surrounded radially by an outer section of the third catheter 12 to provide insulation from an external environment. In some embodiments, an outer surface of the electrode 204 can be flush with an outer surface of the third catheter 12 and can provide an exposed, radially outwardly facing electrode surface. In such instances, a radially inner section of the third catheter 12 can provide insulation from the environment within the lumen of the third catheter 12.

The electrode 204 can include one or more rings, one or more coils or other suitable conductive structures, and can each form at least one surface (e.g., an inner surface or an outer surface) that is exposed and configured for electrical activity or conduction. The electrode 204 can have a fixed inner diameter or size, or a radially expandable inner diameter or size. In some embodiments, the electrode 204 is a "painted" electrode. The electrode can include platinum, platinum alloys (e.g., 92% platinum and 8% tungsten, 90% platinum and 10% iridium), gold, cobalt-chromium, stainless steel (e.g., 304 or 316), nitinol, and combinations thereof, or any suitable conductive materials, metals or alloys.

In some embodiments, the electrode 204 can be a separate expandable member coupled to an outer surface of the third catheter 12, for example a braid, stent, or other conductive element coupled to an outer surface of the distal portion of the third catheter 12. In some embodiments, the electrode can be part of a flow-arrest element such as an expandable braid coupled to an occlusion balloon.

According to some embodiments, the electrode 204 can be electrically connected to the current generator 20 via a conductive lead 205. The conductive lead 205 can extend proximally along or within the wall of the third catheter 12 to or beyond the proximal end of the third catheter 12. The conductive lead 205 can include more than one conductive path extending within the walls of the third catheter 12. According to some embodiments, the conductive lead 205 can form a helical coil along or within at least a portion of the third catheter 12. Alternatively or in combination, the conductive lead 205 can form a braided, woven, or lattice structure along or within at least a portion of the third catheter 12. In some embodiments, the conductive lead 205 can be a conductive element (e.g., a wire, coil, etc.) wrapped around an external surface of the third catheter 12. In such instances, the conductive lead 205 can be coated with an insulative material along at least a portion of its length. The insulative material can be, for example, Parylene, PTFE, or other suitable insulative material.

In some embodiments, the second catheter 13 and/or the first catheter 14 can be similarly equipped with corresponding electrodes instead of or in addition to the third catheter 12 or the core member 11. For example, the second catheter 13 may include an electrode 206 disposed at a distal end region of the second catheter 13. The electrode 206 can be electrically connected to the current generator 20 (FIG. 1A) via a conductive lead 207 which extends proximally along the second catheter 13. The configuration of the electrode 206 and the corresponding conductive lead 207 can be similar to any of the variations described above with respect to the electrode 204 and the conductive lead 205 of the third catheter 12.

In some embodiments, the first catheter 14 includes an electrode 208 disposed at a distal end region of the first catheter 14. The electrode 208 can be electrically connected to the current generator 20 (FIG. 1A) via a conductive lead 209 which extends proximally along the first catheter 14. The configuration of the electrode 208 and the corresponding conductive lead 209 can be similar to any of the variations described above with respect to the electrode 204 and the conductive lead 205 of the third catheter 12.

In various embodiments, the system can include any combination of the electrodes 204, 206, and 208 described above. For example, the system may include the electrode 204 and the corresponding conductive lead 205 of the third catheter 12, while the second catheter 13 and the first catheter 14 may be provided with no electrodes or conductive leads therein. In other embodiments, the system may only include the electrode 206 of the second catheter 13, while the third catheter 12 and the first catheter 14 may be provided with no electrodes or conductive leads therein. In still other embodiments, the system may include only the electrode 208 of the first catheter 14, while the third catheter 12 and the second catheter 13 are provided with no electrodes or corresponding conductive leads therein. In some embodiments, any two of the catheters 12, 13, or 14 can be provided with electrodes and corresponding leads, while the remaining catheter may have no electrode or conductive lead therein.

In the configuration illustrated in FIG. 2A, one or more of electrodes 204, 206, or 208 can be coupled to a negative terminal of the current generator 20, while the interventional element 100 can be coupled to the positive terminal of the current generator 20 via the core member 11. As a result, when voltage is applied at the terminals and the interventional element 100 placed in the presence of blood (or any other electrolytic medium), current flows from the interventional element 100, through the blood or medium, and to the return electrode. The return electrode may a conductive element carried by one or more of the catheters 12, 13, or 14 as described above, or the core member 11, or in some embodiments the return electrode can be an external electrode 29 (FIG. 1A) such as needle or grounding pad.

In some embodiments, one or more catheters carrying an electrode can be used without an electrically coupled interventional element 100. In various embodiments, the interventional element 100 may be omitted altogether (as in FIGS. 6A-6B described below), or the interventional element 100 may be included but may not be electrically coupled to the current generator 20. In such cases, a catheter-based electrode (e.g., the electrode 204 carried by the third catheter 12, the electrode 206 carried by the second catheter 13, or the electrode 208 carried by the first catheter 14) can function as the delivery electrode, and a separate return electrode can be provided either in the form of another catheter-based electrode (either carried by the same catheter or carried by another catheter) or as an external electrode (e.g., a needle or grounding pad). In instances in which a single catheter carries two electrodes, one electrode may be provided on an exterior surface of the catheter while the other electrode may be provided on an inner surface of the catheter. For example, the second catheter 13 may include a delivery electrode in the form of a conductive band disposed on an inner surface of the catheter 13, in addition to a return electrode in the form of a conductive band disposed on an outer surface of the catheter 13.

As described in more detail in FIG. 2B, in some embodiments the return electrode can be integrated into the core member 11 of the treatment system 10, such that the core member 11 carries two separate conductive paths along its length. FIG. 2B is a side schematic cross-sectional view of a portion of the treatment system shown in FIG. 2A, in accordance with some embodiments. As shown in FIG. 2B, the core member 11 includes an elongate conductive shaft 211 and an elongate tubular member 212 having a lumen through which the shaft 211 extends. The shaft 211 has a distal portion 210, and the tubular member 212 has a distal portion 218. Both the shaft 211 and the tubular member 212 are electrically conductive along their respective lengths. In some embodiments, the positions of the shaft 211 and the tubular member 212 are fixed relative to one another. For example, in some embodiments the shaft 211 is not slidable or rotatable with respect to the tubular member 212 such that the core member 11 can be pushed or pulled without relative movement between the shaft 211 and the tubular member 212 and/or other individual components of the core member 11.

In some embodiments, the shaft 211 can be a solid pushwire, for example a wire made of Nitinol, stainless steel, or other metal or alloy. The shaft 211 may be thinner than would otherwise be required due to the additional structural column strength provided by the surrounding tubular member 212. The tubular member 212 can be a hollow wire, hypotube, braid, coil, or other suitable member(s), or a combination of wire(s), tube(s), braid(s), coil(s), etc. In some embodiments, the tubular member 212 can be a laser-cut hypotube having a spiral cut pattern (or other pattern of cut voids) formed in its sidewall along at least a portion of its length. The tubular member 212 can be made of stainless steel (e.g., 304 SS), Nitinol, and/or other alloy. In at least some embodiments, the tubular member 212 can have a laser cut pattern to achieve the desired mechanical characteristics (e.g., column strength, flexibility, kink-resistance, etc.).

The core member 11 can also include an adhesive or a mechanical coupler such as a crimped band or marker band 220 disposed at the distal end of the core member 11, and the marker band 220 can optionally couple the distal end of the core member 11 to the interventional element 100. The marker band 220 can be radiopaque, for example including platinum or other radiopaque material, thereby enabling visualization of the proximal end of the interventional element 100 under fluoroscopy. In some embodiments, additional radiopaque markers can be disposed at various locations along the treatment system 10, for example along the shaft 211, the tubular member 212, or the interventional element 100 (e.g., at the distal end, or along the length, of the interventional element 100).

In at least some embodiments, the core member 11 also includes a first insulating layer or material 222 extending between the shaft 211 and the surrounding tubular member 212. The first insulating material 222 can be, for example, PTFE (polytetrafluoroethylene or TEFLON™) or any other suitable electrically insulating coating (e.g., polyimide, oxide, ETFE-based coatings, or any suitable dielectric polymer). In some embodiments, the first insulating material 222 extends along substantially the entire length of the shaft 211. In some embodiments, the first insulating material 222 separates and electrically insulates the shaft 211 and the tubular member 212 along the entire length of the tubular member 212. In some embodiments, the first insulating material 222 does not cover the proximal-most portion of the shaft 211, providing an exposed region of the shaft to which the current generator 20 (FIG. 1A) can be electrically coupled. In some embodiments, for example, the first insulating material 222 terminates proximally at the proximal terminus of the shaft, and the current generator 20 (FIG. 1A) can electrically couple to the shaft 211 at its proximal terminus, for example using a coaxial connector.

The core member 11 can additionally include a second insulating layer or material 224 surrounding the tubular member 212 along at least a portion of its length. The second insulating layer 224 can be, for example, PTFE or any other suitable electrically insulative coating (e.g., polyimide, oxide, ETFE based coatings or any suitable dielectric polymer). In some embodiments, the distal portion 218 of the tubular member 212 is not covered by the second insulating layer 224, leaving an exposed conductive surface at the distal portion 218. In some embodiments, the length of the exposed distal portion 218 of the tubular member 212 can be at least (or equal to) 1, 2, 3, 4, 5, 6, or more inches. In some embodiments, the length of the exposed distal portion 218 of the tubular member 212 can be between at least 1 and 10 inches, or between 2 inches and 8 inches, or between 3 and 7 inches, or between 4 and 6 inches, or about 5 inches. This exposed portion of the distal portion 218 of the tubular member 212 provides a return path for current supplied to the delivery electrode (e.g. the entirety or a portion of the interventional element 100), as described in more detail below. In some embodiments, the second insulating material 224 does not cover the proximal-most portion of the tubular member 212, providing an exposed region of the tubular member 212 to which the current generator 20 (FIG. 1A) can be electrically coupled. In some embodiments, the second insulating material 224 proximally terminates at the proximal terminus of the tubular member 212, and the current generator 20 can electrically couple to the tubular member 212 at its proximal terminus, for example using a coaxial connector.

The core member 11 can also include a retraction marker in the proximal portion of the tubular member 212. The retraction marker can be a visible indicator to guide a clinician when proximally retracting an overlying catheter with respect to the core member 11. For example, the retraction marker can be positioned such that when a proximal end of the overlying catheter is retracted to be positioned at or near the retraction marker, the distal portion 218 of the tubular member 212 is positioned distally beyond a distal end of the catheter. In this position, the exposed distal portion 218 of the tubular member 212 is exposed to the surrounding environment (e.g., blood, tissue, etc.), and can serve as a return electrode for the core member 11.

The proximal end of the shaft 211 can be electrically coupled to the positive terminal of the current generator 20, and the proximal end of the tubular member 212 can be electrically coupled to the negative terminal of the current generator 20. During operation, the treatment system 10 provides an electrical circuit in which current flows from the positive terminal of the current generator 20, distally through the shaft 211, the interventional element 100, and the surrounding media (e.g., blood, tissue, thrombus, etc.) before returning back to the exposed distal portion 218 of the tubular member, proximally through the tubular member 212, and back to the negative terminal of the current generator 20 (FIG. 1A).

As noted above, the current generator 20 (FIG. 1A) can include a power source and either a processor coupled to a memory that stores instructions for causing the power source to deliver electric current according to certain parameters, or hardwired circuit elements configured to deliver electric current according to the desired parameters. The current generator 20 may be integrated into the core member 11 or may be removably coupled to the core member 11, for example via clips, wires, plugs or other suitable connectors. Particular parameters of the energy provided by the current generator 20 are described in more detail below with respect to FIGS. 7A-7E.

In certain embodiments, the polarities of the current generator 20 can be switched, so that the negative terminal is electrically coupled to the shaft 211 and the positive terminal is electrically coupled to the tubular member 212. This can be advantageous when, for example, attempting to attract predominantly positively charged material to the interventional element 100, or when attempting to break up a clot rather than grasp it with an interventional element. In some embodiments alternating current (AC) signals may be used rather than DC. In certain instances, AC signals may advantageously help break apart a thrombus or other material.

II. Select Embodiments of Interventional Elements for Use with the Treatment Systems Disclosed Herein Referring still to FIGS. 2A and 2B, in some embodiments the interventional element 100 can be a metallic or electrically conductive thrombectomy device. The interventional element 100 can have a low-profile, constrained or compressed configuration (not shown) for intravascular delivery to the treatment site within the third catheter 12, and an expanded configuration for securing and/or engaging clot material and/or for restoring blood flow at the treatment site. The interventional element 100 has a proximal portion 100a that may be coupled to the core member 11 and a distal portion 100b. The interventional element 100 further includes an open cell framework or body 226 and a coupling region 228 extending proximally from the body 226. In some embodiments, the body 226 of the interventional element 100 can be generally tubular (e.g., cylindrical), and the proximal portion 100a of the interventional element 100 can taper proximally to the coupling region 228.

In various embodiments, the interventional element 100 can take any number of forms, for example a removal device, a thrombectomy device, or other suitable medical device. For example, in some embodiments the interventional element 100 may be a stent and/or stent retriever, such as Medtronic's Solitaire™ Revascularization Device, Stryker Neurovascular's Trevo® ProVue™ Stentriever, or other suitable devices. In some embodiments, the interventional element 100 may be a coiled wire, a weave, and/or a braid formed of a plurality of braided filaments. Examples of suitable interventional elements 100 include any of those disclosed in U.S. Pat. No. 7,300,458, filed Nov. 5, 2007, U.S. Pat. No. 8,940,003, filed Nov. 22, 2010, U.S. Pat. No. 9,039,749, filed Oct. 1, 2010, and U.S. Pat. No. 8,066,757, filed Dec. 28, 2010, each of which is incorporated by reference herein in its entirety.

In some embodiments, the interventional element 100 is a mesh structure (e.g., a braid, a stent, etc.) formed of a superelastic material (e.g., Nitinol) or other resilient or self-expanding material configured to self-expand when released from the third catheter 12. The mesh structure may include a plurality of struts 101 and open spaces 103 between the struts 101. In some embodiments, the struts 101 and spaces 103 may be situated along the longitudinal direction of the interventional element 100, the radial direction, or both.

As depicted in FIG. 2A, the interventional element 100 may comprise a working length WL portion and a non-working length NWL portion. The portion of the interventional element 100 in the working length WL may be configured to interlock, capture, and/or engage a thrombus. The portion of the interventional element 100 in the non-working length NWL may contact thrombotic material in use, but is configured to perform a function that renders it ineffective or less effective than the working length WL portion for interlocking, capturing, and/or engaging with a thrombus. In some embodiments, such as that shown in FIG. 2A, a distal terminus of the working length WL portion is proximal of the distal terminus of the interventional element 100 (i.e., the working length WL portion is spaced apart from the distal terminus of the interventional element 100), and the non-working length NWL portion is disposed between the working length WL and the band 220 and/or the distal end of the core member 11.

In some embodiments, the non-working length NWL portion of the interventional element 100 can be coated with a non-conductive or insulative material (e.g., Parylene, PTFE, or other suitable non-conductive coating) such that the coated region is not in electrical contact with the surrounding media (e.g., blood). As a result, the current carried by the core member 11 to the interventional element 100 is only exposed to the surrounding media along the working length WL portion of the interventional element 100. This can advantageously concentrate the electrically enhanced attachment effect along the working length WL of the interventional element 100, where it is most useful, and thereby combine both the mechanical interlocking provided by the working length WL and the electrical enhancement provided by the delivered electrical signal. In some embodiments, a distal region of the interventional element 100 (e.g. distal of the working length WL) may likewise be coated with a non-conductive material (e.g., Parylene, PTFE, or other suitable non-conductive coating), leaving only a central portion or the working length WL of the interventional element 100 having an exposed conductive surface.

Figure 3A:
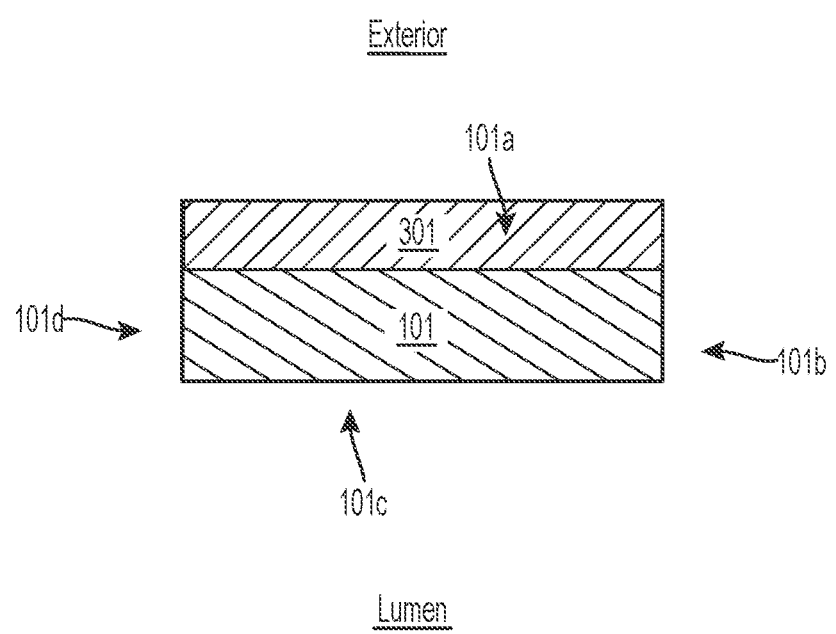
FIG. 3A illustrates an interventional element with one or more coatings in accordance with embodiments of the present technology.

In some embodiments, the interventional element 100 may include a conductive material positioned on some or all of its outer surface. The conductive material, for example, can be gold and/or another suitable conductor that has a conductivity greater than (or a resistivity less than) that of the material comprising the interventional element 100. The conductive material may be applied to the interventional element 100 via electrochemical deposition, sputtering, vapor deposition, dip-coating, and/or other suitable means. FIG. 3A, for example, is a cross-sectional view of a strut 101 of the interventional element 100 having a conductive material 301 disposed thereon. Although the strut 101 shown in FIG. 3A has a generally square or rectangular cross-sectional shape, in some embodiments the interventional element 100 includes one or more struts or filaments having other cross-sectional shapes (e.g., circle, oval, etc.).

As shown in FIG. 3A, the strut 101 has a surface comprised of an outer portion 101a facing away from a lumen of the interventional element 100, an inner portion 101c facing toward the lumen, and side portions 101b and 101d extending between the outer and inner portions 101a, 101c. In some embodiments, such as that shown in FIG. 3A, the conductive material 301 may be disposed only at the outer portion 101a of the strut 101 and the inner and side portions 101b-d may be exposed or otherwise not in contact with or covered by the conductive material 301. In some embodiments, the conductive material 301 may be disposed only on the inner portion 101c of the surface, only on one of the side portions 101b, 101d, or on any combination of the surface portions 101a-d.

In some aspects of the present technology, the conductive material 301 is disposed only on the working length WL portion of the interventional element 100 such that the proximal and distal portions 100a, 100b of the interventional element 100 are exposed. Because the conductive material 301 has a much lower resistance than the underlying material comprising the interventional element 100, current delivered to the interventional element 100 concentrates along the working length WL portion. In several of such embodiments, the conductive material 301 may be disposed only on the outer portion 101a of the strut surface along the working length WL portion. In other embodiments, the conductive material 301 may be disposed on all or a portion of the strut surface along all or a portion of the length of the interventional element 100.

In some embodiments, a first portion of the interventional element 100 is covered by the conductive material 301 and a second portion of the interventional element 100 is covered by an insulative or dielectric material (e.g., Parylene). For example, in some embodiments the outer portion 101a of the strut surface is covered by a conductive material while an inner portion 101c of the strut surface is covered by an insulative material. In some embodiments, the working length WL portion of the interventional element 100 may be covered by a conductive material while the non-working length NWL portion is covered by an insulative material. In some embodiments, the conductive material 301 may be disposed on all or a portion of the strut surface along all or a portion of the length of the interventional element 100, and the insulative material may be disposed on those portions of the strut surface and/or working length not covered by the conductive material.

Figure 3B:
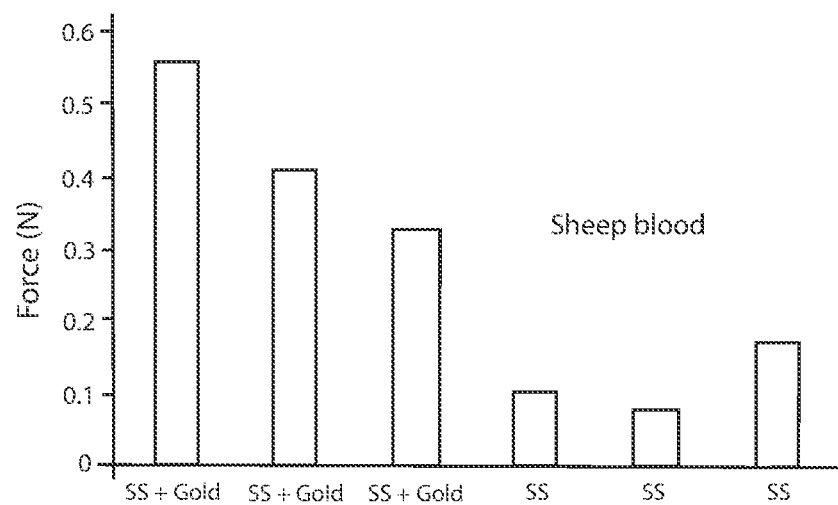
FIGS. 3B and 3C are charts showing clot detachment forces for interventional elements coated with a conductive material and for non-coated interventional elements, in accordance with the present technology.
Figure 3C:
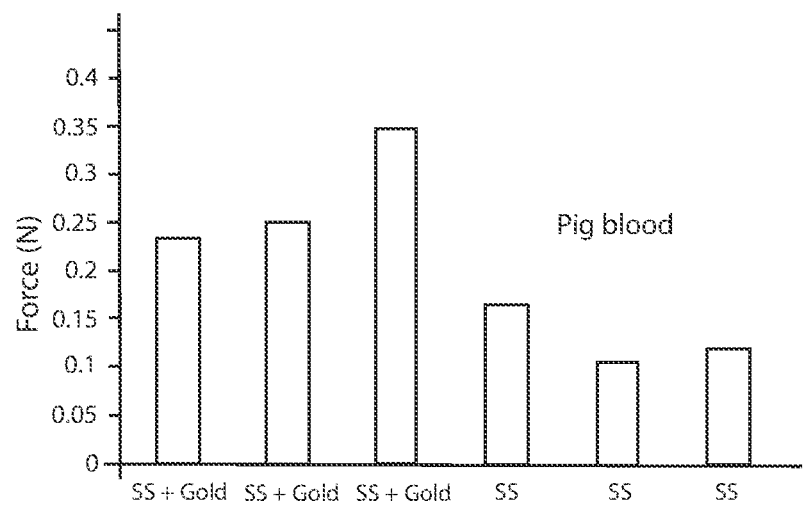

FIGS. 3B and 3C demonstrate the improved adhesion strength between clot material and the interventional element 100 as a result of the conductive material. The charts of FIGS. 3B and 3C, for example, show detachment forces for gold-coated and non-coated ("SS") interventional elements 100 that received electric current while exposed to sheep's or pig's blood, respectively. For these experiments, a blood clot was manufactured by mixing fibrinogen, blood, thrombin and calcium chloride. A representative interventional element was immersed or deployed in contact with the blood clot to mimic clinical deployment and positive charge was applied to it for a specified duration. The whole assembly was immersed in blood and flow was applied at 150 mL/min. The composition of the manufactured blood clot and the parameters of the applied energy (e.g., duration, amplitude, etc.) were generally the same for all samples in both experiments. The assembly (blood clot and interventional element) was then removed from the experimental setup and the blood clot was detached from the interventional element using a lap-shear test with an Instron. The detachment force was measured and is reported in the charts. In both charts, the average detachment force for the gold-coated samples is at least two times the average detachment force for the non-coated samples.

III. Select Methods of Use

Figure 4A:
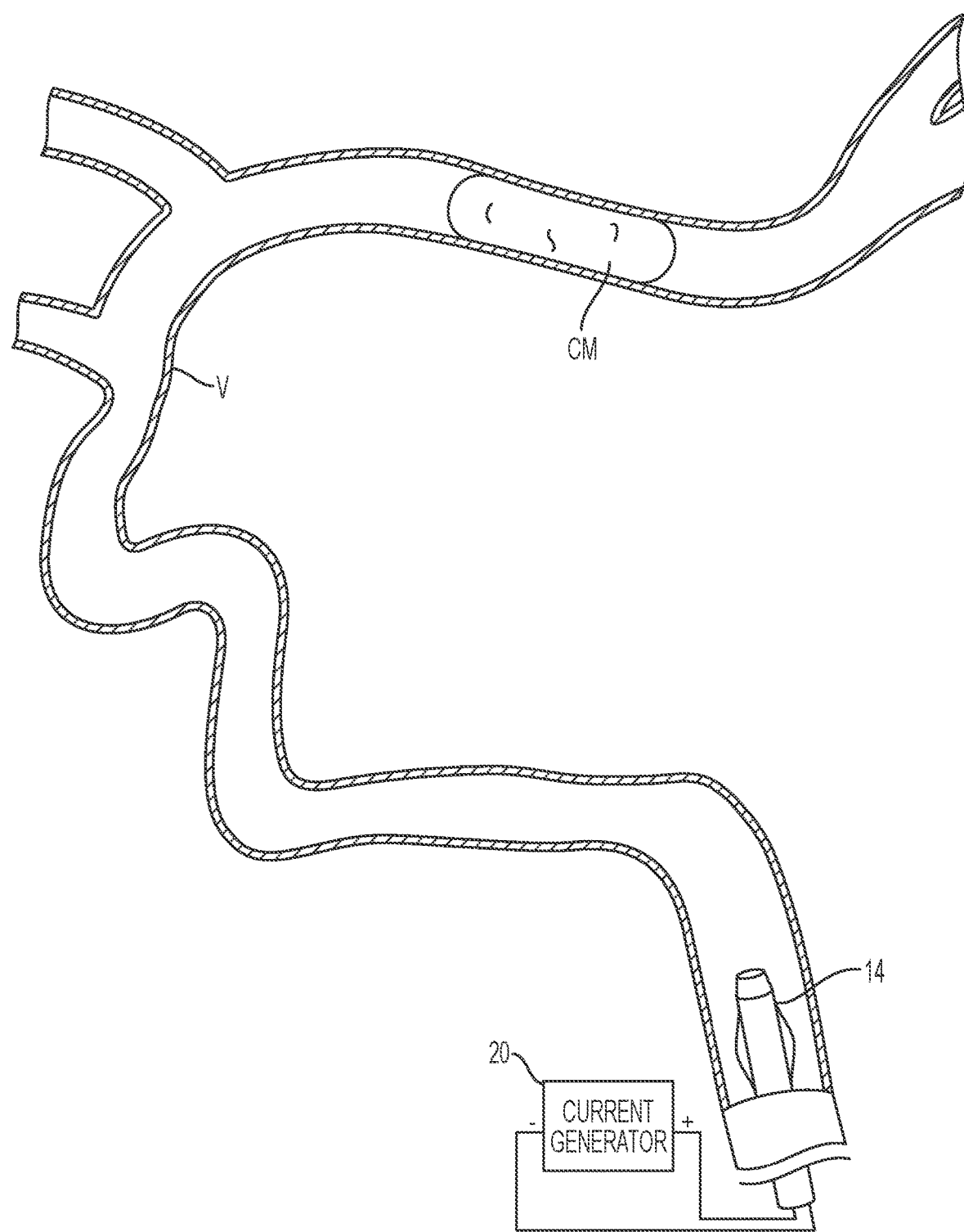
FIGS. 4A-4G illustrate a method of removing clot material from a blood vessel lumen using an electrically enhanced treatment system.
Figure 4B:
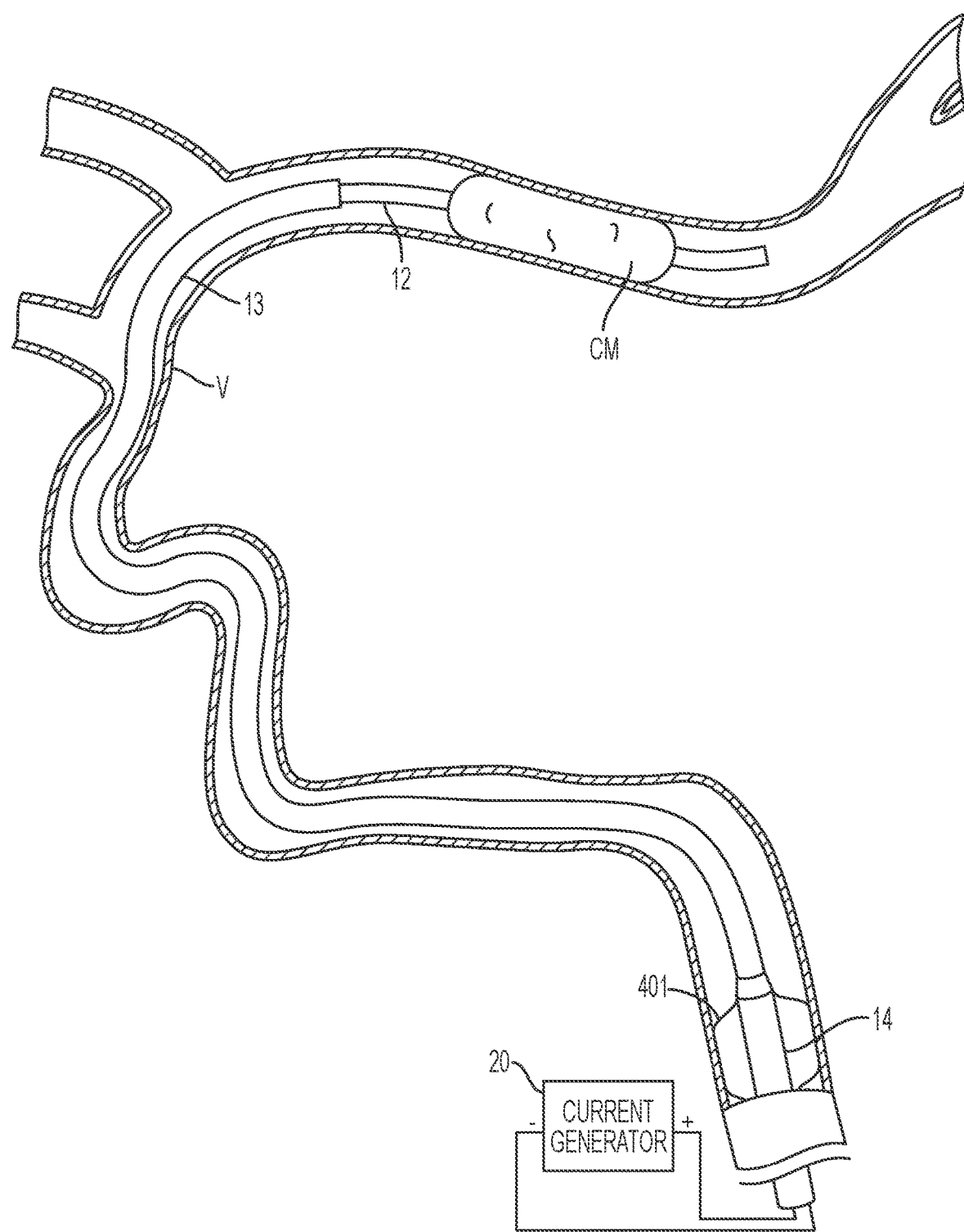

FIGS. 4A-4G illustrate a method of removing clot material CM from the lumen of a blood vessel V using the treatment system 10 of the present technology. As shown in FIG. 4A, the first catheter 14 can be advanced through the vasculature and positioned within the blood vessel such that a distal portion of the first catheter 14 is proximal of the clot material CM. As shown in FIG. 4B, the second catheter 13 may be advanced through the first catheter 14 until a distal portion of the second catheter 13 is at or proximal to the clot material CM. Next, the third catheter 12 may be advanced through the second catheter 13 so that a distal portion of the third catheter 12 is positioned at or near the clot material CM. In some embodiments, the third catheter 12 may be positioned such that a distal terminus of the third catheter 12 is distal of the clot material CM. The interventional element 100 may then be advanced through the third catheter 12 in a low-profile configuration until a distal terminus of the interventional element 100 is at or adjacent the distal terminus of the third catheter 12.

Figure 4C:
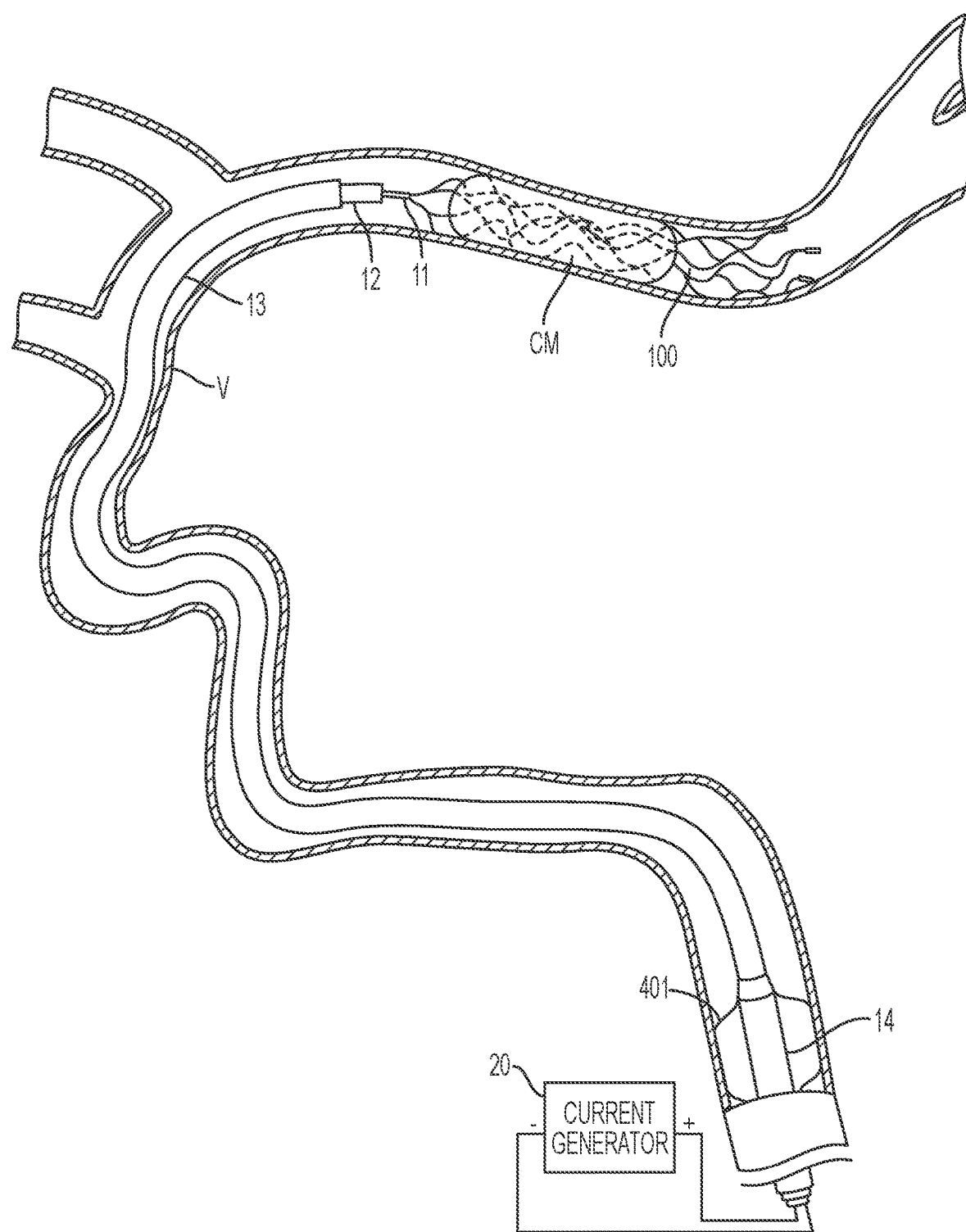

As shown in FIG. 4C, the third catheter 12 may be withdrawn proximally relative to the interventional element 100 to release the interventional element 100, thereby allowing the interventional element 100 to self-expand within the clot material CM. As the interventional element 100 expands, the interventional element 100 engages and/or secures the surrounding clot material CM, and in some embodiments may restore or improve blood flow through the clot material CM by pushing open a blood flow path therethrough. In some embodiments, the interventional element 100 may be expanded distal of the clot material CM such that no portion of the interventional element 100 is engaging the clot material CM while the interventional element 100 is in the process of expanding toward the vessel wall. In some embodiments, the interventional element 100 is configured to expand into contact with the wall of the vessel V, or the interventional element 100 may expand to a diameter that is less than that of the blood vessel lumen such that the interventional element 100 does not engage the entire circumference of the blood vessel wall.

Once the interventional element 100 has been expanded into engagement with the clot material CM, the interventional element 100 may grip the clot material CM by virtue of its ability to mechanically interlock with the clot material CM. The current generator 20, which is electrically coupled to the proximal end of the core member 11, can deliver a current to the interventional element 100 before or after the interventional element 100 has been released from the third catheter 12 into the blood vessel and/or expanded into the clot material CM. The interventional element 100 can be left in place or manipulated within the vessel V for a desired time period while the electrical signal is being delivered. Positive current delivered to the interventional element 100 can attract negatively charged constituents of the clot material CM, thereby enhancing the grip of the interventional element 100 on the clot material CM. This allows the interventional element 100 to be used to retrieve the clot material CM with reduced risk of losing grip on the thrombus or a piece thereof, which can migrate downstream and cause additional vessel blockages in areas of the brain that are more difficult to reach.

In some methods of the present technology, a guidewire (not shown) may be advanced to the treatment site and pushed through the clot material CM until a distal portion of the guidewire is distal of the clot material CM. The guidewire may be advanced through one or more of the catheters 12-14 and/or one or more of the catheters 12-14 may be advanced over the guidewire. The guidewire may be insulated along at least a portion of its length (e.g., with parylene, PTFE, etc.), with exposed portions permitting electrical communication with the current generator 20 and the interventional element 100. For example, in some embodiments a distal portion of the guidewire may be exposed and the guidewire may be positioned at the treatment site such that the exposed portion of the guidewire is distal of the clot material CM. A proximal end of the guidewire may be coupled to the current generator such that the exposed portion of the guidewire functions as a return electrode. In some embodiments, the guidewire may be coupled to the positive terminal of the power source and the exposed portion functions as a delivery electrode. The guidewire may be used as a delivery or return electrode with any delivery or return electrode carried by any component of the treatment system (e.g., one or more of the first-third catheters 14, 13, 12, the interventional element 100, etc.).

Figure 4D:
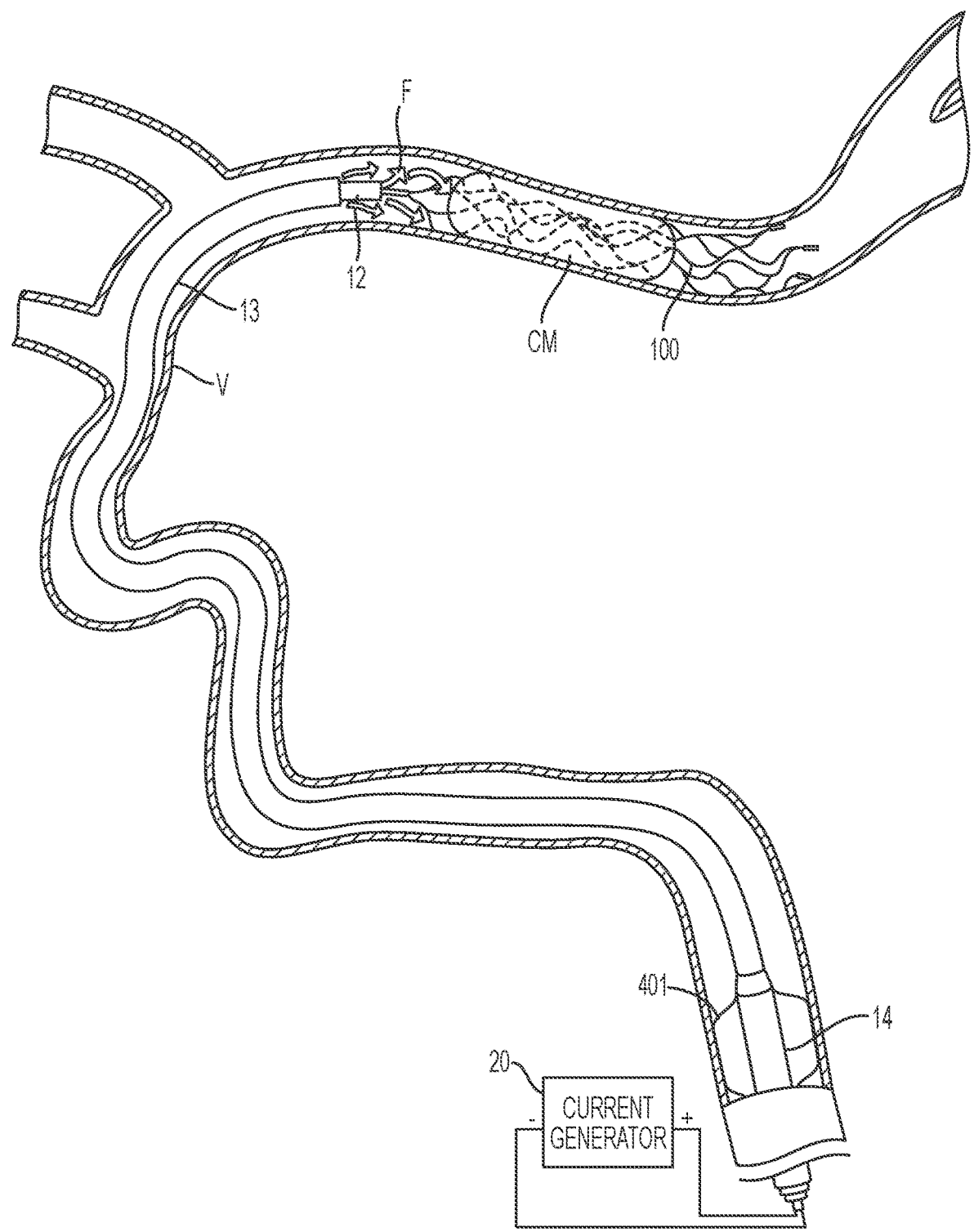
Figure 4E:
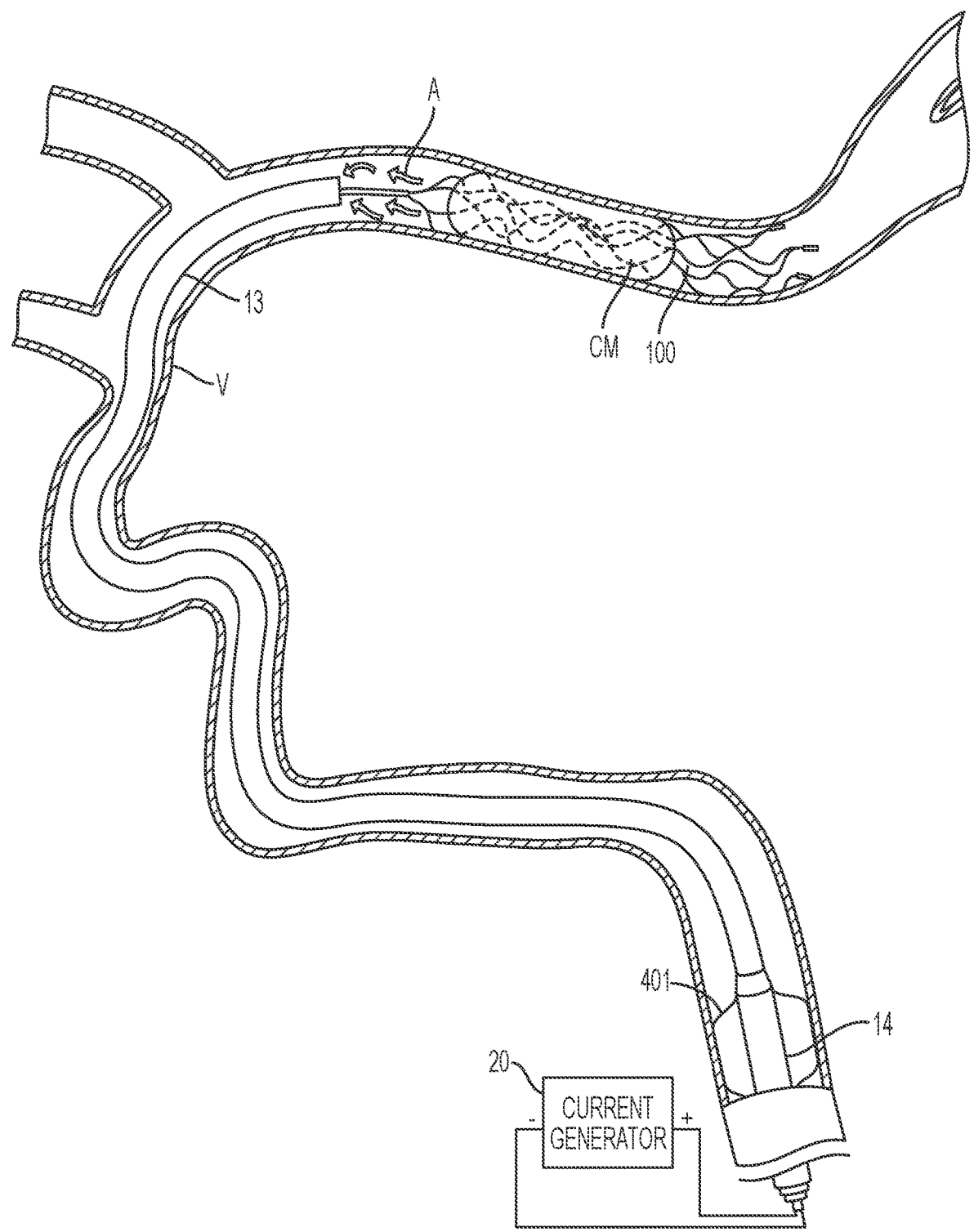
Figure 4F:
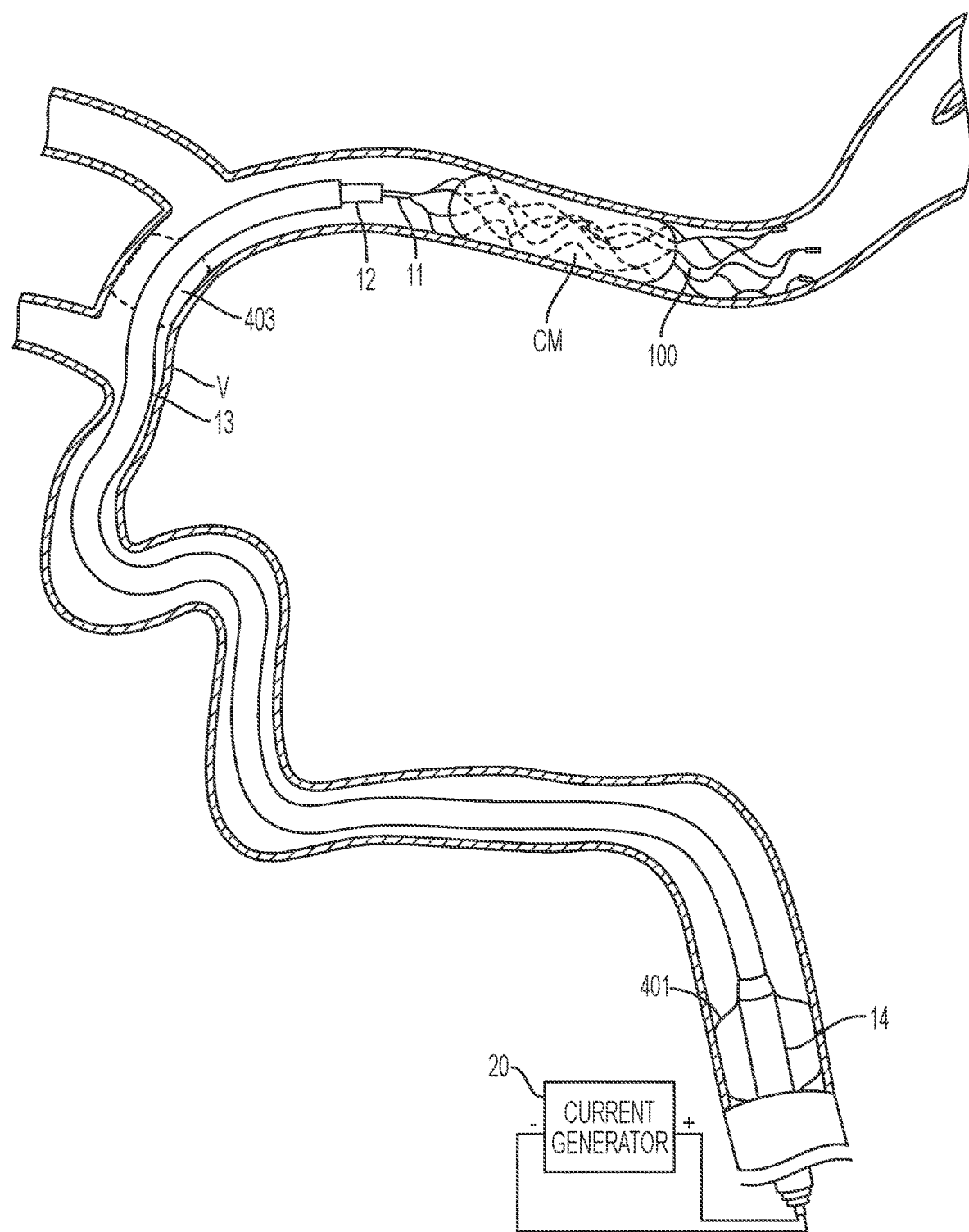

FIGS. 4D-4F illustrate optional processes that may be performed before, during, and/or after deployment of the interventional element 100. With reference to FIG. 4D, in some methods fluid F may be delivered to the treatment site via the second catheter 13 and/or third catheter 12 while current is being delivered to the interventional element 100. Fluid delivery may occur before or while the interventional element 100 is engaging the thrombus, and may coincide with the entire duration of current delivery or just a portion thereof.

Figure 5:
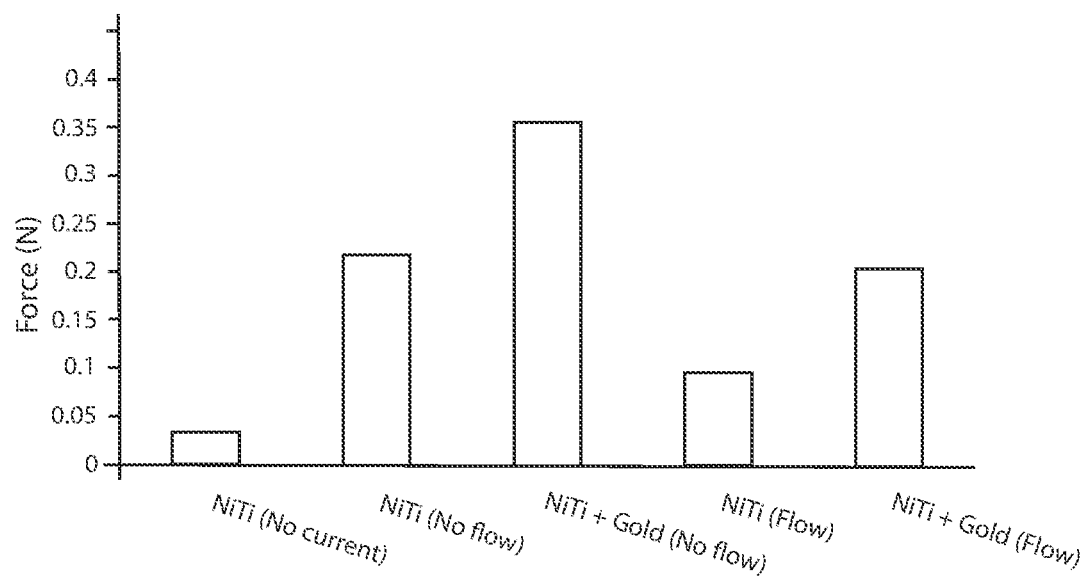
FIG. 5 is a chart showing clot detachment forces for different interventional element embodiments under different environments.

FIG. 5 is a chart showing clot detachment forces for different interventional elements of the present technology under different environmental conditions (as indicated along the x-axis). For these experiments, a blood clot was manufactured by mixing fibrinogen, blood, thrombin and calcium chloride. A representative interventional element was immersed or deployed in contact with the blood clot to mimic clinical deployment and positive charge was applied to it for a specified duration. The whole assembly was immersed in blood and flow was applied at 150 mL/min ("Flow") or 0 mL/min ("No Flow"). The composition of the manufactured blood clot and the parameters of the applied energy (e.g., duration, amplitude, etc.) were generally the same for all samples in both experiments. The assembly (blood clot and interventional element) was then removed from the experimental setup and the blood clot was detached from the interventional element using a lap-shear test with an Instron. The detachment force was measured and is reported in FIG. 5. As demonstrated by the chart shown in FIG. 5, the inventors have observed that the presence of blood flow at the treatment site reduces adhesion between an electrically charged interventional element and a blood clot by approximately two-fold (see "NiTi (No Flow)" vs. "NiTi (Flow)", and "NiTi+Gold (No Flow)" vs. "NiTi+Gold (Flow)".) FIG. 5 also demonstrates that the adhesion forces for a gold-coated interventional element are at least two times the adhesion forces for a non-coated interventional element (see "NiTi (No Flow)" vs. "NiTi+Gold (No Flow)", and "NiTi (Flow)" vs. "NiTi+Gold (Flow)").

Although the presence of blood flow at the treatment site is believed to reduce adhesion between an electrically charged interventional element and a blood clot, the inventors have also observed that infusion of a fluid F having a higher ion concentration than blood increases the electrical conductivity at the treatment site, thereby providing an improved environment for electrically enhanced clot adhesion as compared to the presence of blood alone. The same experimental setup described above was used and the blood was replaced by saline with flow at 150 mL/min. The inventors observed that the adhesive force was approximately 35% higher when saline was infused at the treatment site than it was in the presence of autologous blood alone. In some embodiments, infusion of the fluid F may occur in the presence of blood flow, or without blood flow present (the latter condition being induced, for example, by inflation of the expandable element 401 on the first catheter 14). Suitable fluids include, for example, saline, contrast solution, and other fluids having a higher ion concentration than blood. Additionally, the delivery of fluid F at the treatment site may also reduce new clot formation on the interventional element 100, which may occur in the presence of blood and direct or pulsatile electric current.

Referring now to FIG. 4E, in some instances aspiration may be applied to the treatment site via the second catheter 13. For example, following deployment of the interventional element 100, the third catheter 12 can be retracted and removed from the lumen of the second catheter 13. The treatment site can then be aspirated via the second catheter 13, for example via a suction source such as a pump or syringe coupled to a proximal portion of the second catheter 13. In some embodiments, following expansion of the interventional element 100, the treatment site is aspirated concurrently with supplying electrical energy to the interventional element 100 via the current generator 20. By combining aspiration with the application of electrical energy, any newly formed clots (e.g., any clots formed that are attributable at least in part to the application of electrical energy), or any clot pieces that are broken loose during the procedure, can be pulled into the second catheter 13, thereby preventing any such clots from being released downstream of the treatment site. As a result, concurrent aspiration may permit the use of higher power or current levels delivered to the interventional element 100 without risking deleterious effects of new clot formation. Additionally, aspiration can capture any gas bubbles formed along the interventional element 100 or marker band 220 (FIG. 2A) during application of electrical energy to the interventional element 100, which can improve patient safety during the procedure.

In some embodiments, aspiration is applied while the interventional element 100 is retracted into the second catheter 13. Aspiration at this stage can help secure the clot material CM within the second catheter 13 and prevent any dislodged portion of the clot material CM from escaping the second catheter 13 and being released back into the vessel V. In various embodiments, the treatment site can be aspirated continuously before, during, or after delivering electrical signals to the interventional element 100 as well as before, during, or after retraction of the interventional element 100 into the second catheter 13.

With reference to FIGS. 4B-4F, at any time before, during, and/or after deployment of the interventional element 100, a flow arrest element may be deployed within the blood vessel proximal of the clot material CM to partially or completely arrest blood flow to the treatment site. For example, as shown in FIGS. 4B-4F, the first catheter 14 may be a balloon guide catheter having a balloon 401 at its distal portion. The balloon 401 may be configured to inflate or expand into apposition with the surrounding blood vessel wall, thereby at least partially arresting blood flow distal to the balloon 401. In some embodiments, the flow arrest element can have other forms or configurations suitable for partially or completely arresting blood flow within the vessel V.

In some methods, the flow arrest element may be deployed at a location along the blood vessel proximal of the clot material CM (for example, at a proximal portion of the internal carotid artery) and may remain inflated as the interventional element 100 is deployed and eventually withdrawn to remove the thrombus. For example, FIGS. 4B-4F show the balloon 401 blocking flow from a portion of the artery proximal of the balloon toward the interventional element 100 and treatment area, while the second catheter 13 and third catheter 12 are positioned at the treatment site (FIG. 4B), while the interventional element 100 is expanded within the clot material CM (FIG. 4C), while fluid is infused at the treatment site (FIG. 4D), and while aspiration is applied at the treatment site (FIG. 4E). Although the balloon 401 is shown in an expanded state in each of FIGS. 4B-4F, it will be appreciated that the balloon 401 may be in an unexpanded state and/or deflated at any time throughout the procedure to allow blood flow.

As shown in FIG. 4F, in some embodiments the flow arrest element may be a balloon 403 coupled to the second catheter 13 (such as a distal access catheter). In such embodiments, the first catheter 14 may not include a flow arrest element such that flow arrest is achieved via deployment of the flow arrest element coupled to the second catheter 13. For example, in such embodiments, the first catheter 14 may be a sheath or support catheter. The balloon 403 may be inflated at a location distal of the distal end of the first catheter 14, closer to the thrombus. In some methods, the flow arrest element may be deflated and inflated several times throughout the procedure.

At least while the interventional element 100 is deployed and engaging the thrombus CM, electric current may be delivered to the interventional element 100 to positively charge the interventional element 100, thereby enhancing clot adhesion to the interventional element 100. As previously discussed with reference to FIG. 5, the inventors have observed improved electrically enhanced clot adhesion in the absence of blood flow. As such, it may be especially beneficial to arrest flow (e.g., via a flow arrest element on the first or second catheter 14, 13) while the interventional element 100 is charged, and while expanding the interventional element 100 within the thrombus and/or when withdrawing the thrombus proximally.

Figure 4G:
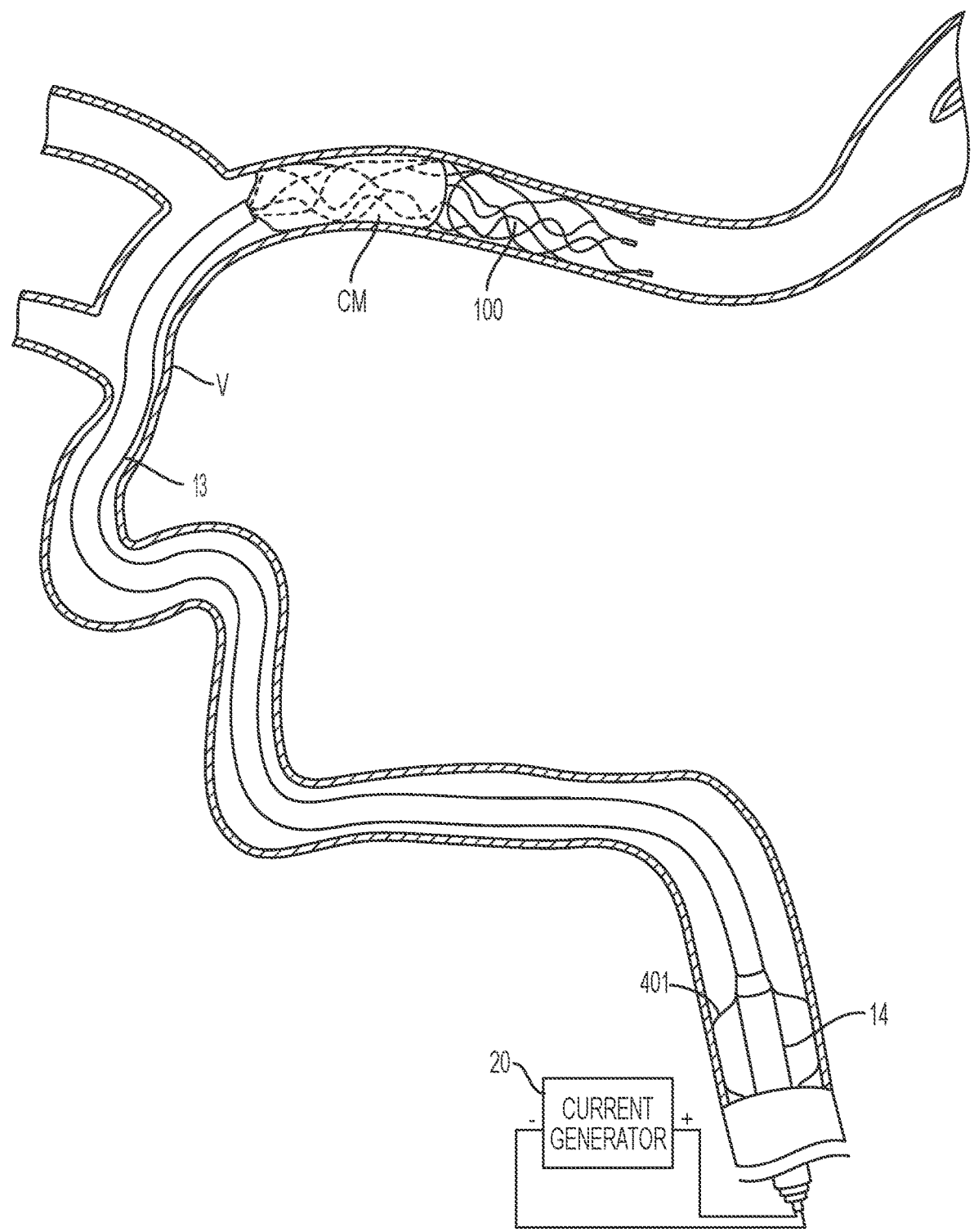

With reference to FIG. 4G, while the interventional element 100 is engaged with the clot material CM, the clot material CM can be removed. For example, the interventional element 100, with the clot material CM gripped thereby, can be retracted proximally (for example, along with the second catheter 13 and, optionally, the third catheter 12). The second catheter 13, interventional element 100, and associated clot material CM may then be withdrawn from the patient, optionally through one or more larger surrounding catheters. During this retraction, the interventional element 100 can grip the clot material CM electrically and/or electrostatically, e.g., via the application of current from a current generator as discussed herein. (As used herein with reference to gripping or retrieving thrombus or other vascular/luminal material, or to apparatus for this purpose, "electrical" and its derivatives will be understood to include "electrostatic" and its derivatives.) Accordingly, the interventional element 100 can maintain an enhanced or electrically and/or electrostatically enhanced grip on the clot material CM during retraction. In other embodiments, the current generator 20 may cease delivery of electrical signals to the interventional element 100 prior to retraction of the interventional element 100 with respect to the vessel V. In some embodiments, the interventional element 100 and clot material CM form a removable, integrated thrombus-device mass wherein the connection of the thrombus to the device is electrically enhanced, e.g. via the application of current as discussed herein.

Figure 6A:
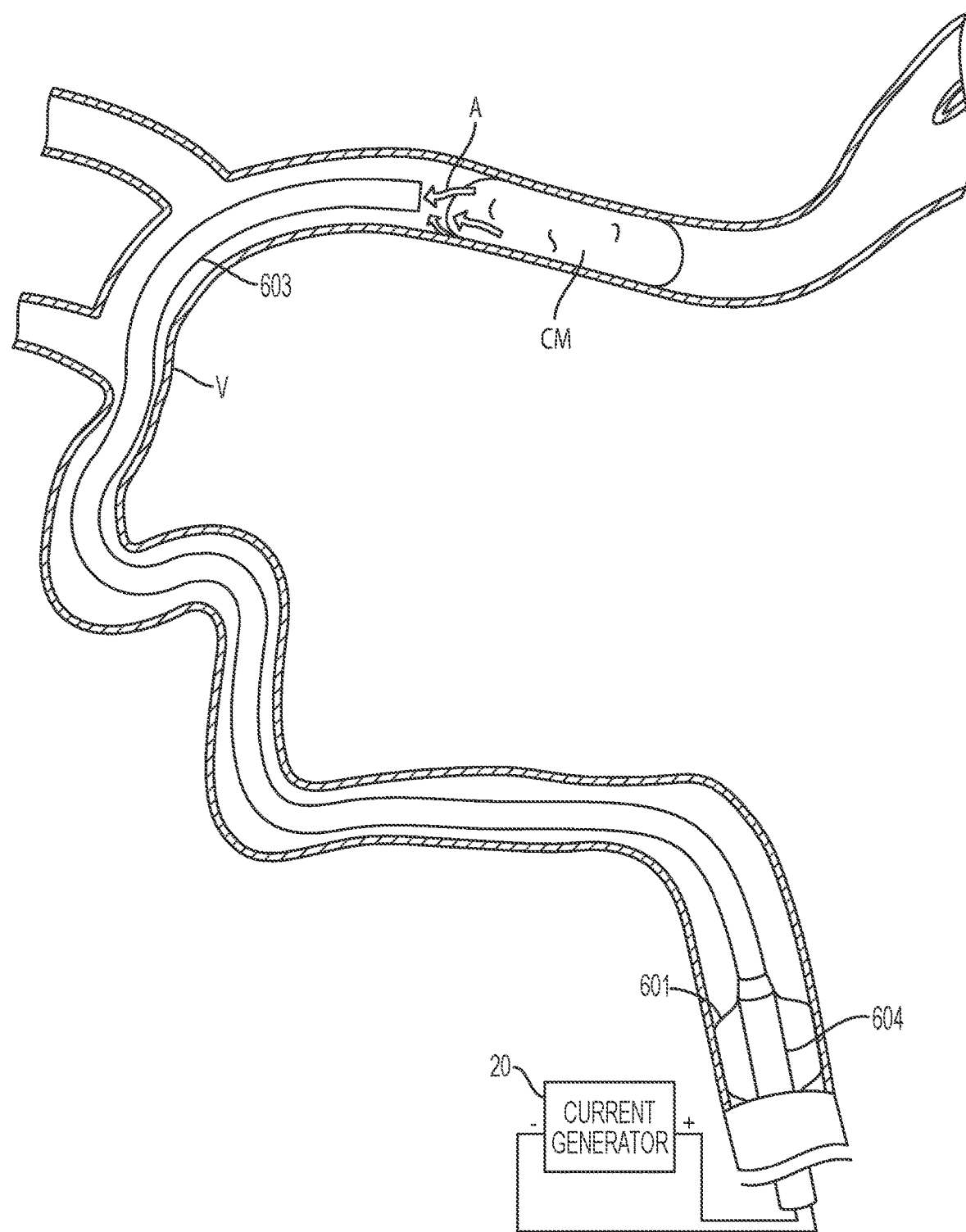
FIGS. 6A-6B illustrate a method of removing clot material from a blood vessel lumen using electrically enhanced aspiration.
Figure 6B:
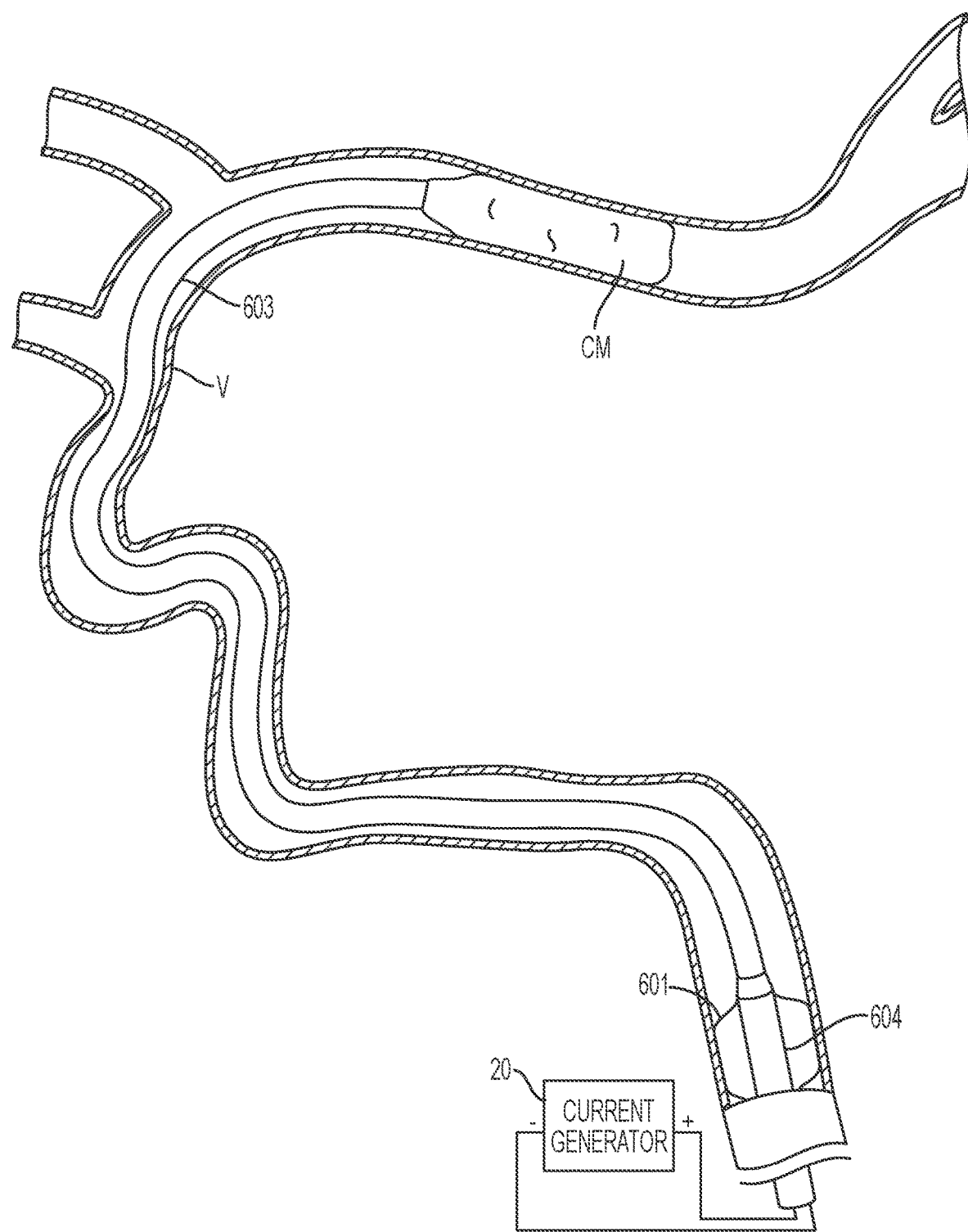

FIGS. 6A-6B illustrates another method of removing clot material from the lumen of a blood vessel V using embodiments of the present technology. As shown in FIG. 6A, a catheter 603 (such as second catheter 13) may be advanced through a vessel V to a position adjacent to clot material CM. The catheter 603 can be advanced through a surrounding catheter 604, for example a balloon-guide catheter having a balloon 601 or other element configured to expand into contact with the vessel wall to secure the catheter 604 in position against the wall of the vessel V and/or to partially or completely arrest flow. In other embodiments, a surrounding sheath or support catheter can be used in place of the catheter 604. In still other embodiments, the catheter 604 can be omitted and the catheter 603 can be advanced directly through the vessel V to the treatment site.

While in the position shown in FIG. 6A, negative pressure can be supplied to the catheter 603 to aspirate the area adjacent to the clot material CM. For example, the catheter 603 can be fluidically coupled to the suction source 25 (FIG. 1A) at a proximal portion of the catheter 603. Additionally, electrical signals can be supplied to the catheter 603 via the current generator 20 to electrically charge a distal portion of the catheter 603. For example, as described above with respect to FIG. 2A, in some embodiments the catheter 603 can be generally similar to second catheter 13 and can include a first electrode 206 disposed at its distal portion. The first electrode can be any electrically conductive element, for example a conductive band extending around an inner or outer surface of the catheter 603, a stent engaged with an inner surface of the second catheter 603, etc. The first electrode can be electrically coupled to a conductive lead that extends proximally along the catheter 603 and is coupled at its proximal end to the positive terminal of current generator 20. The conductive lead can be, for example, a wire, coil, or other conductive element carried by and/or coupled to the catheter 603. In some embodiments, the conductive lead is embedded within a wall of the second catheter 603. In other embodiments, the conductive lead is disposed along an external surface of the catheter 603 (e.g., helically wound around the outer surface of the catheter 603 along its length). The conductive lead can be covered with insulative material along a portion of its length, for example parylene, PTFE, or other suitable insulative coating.

The negative terminal of the current generator 20 can be coupled to a return electrode to complete the electrical circuit with the first electrode disposed on the catheter 603. In some embodiments, the return electrode can be an external electrode (e.g., a needle or a grounding pad coupled to the patient's skin). In other embodiments, the return electrode can be carried by a separate catheter, for example the electrode 208 of the catheter 604 shown in FIG. 2A. In some embodiments, the return electrode can be carried by the catheter 603 at a position spaced apart from the first electrode. For example, the first electrode can be a conductive element such as a band or ring disposed at a position spaced apart from the first electrode. In some embodiments, the first electrode may be exposed along a radially inner surface of the catheter 603, while the return electrode may be exposed along a radially outer surface of the catheter 603. In some embodiments, the return electrode can be a separate expandable member coupled to an outer surface of the catheter 603 (e.g., the balloon 403 of FIG. 4G or other expandable member having a conductive element such as a metallic braid therein).

When the first and second electrodes are coupled to the positive and negative terminals, respectively, of the current generator 20, the distal end of the catheter 603 becomes positively charged and attracts negatively charged constituents in the blood and clot material CM. This electrical attraction promotes movement of the clot material CM into the catheter 603, adhesion of the clot material CM to the inner surface of the catheter 603, and retention of the clot material CM in the lumen of the catheter 603.

In various embodiments, aspiration can be performed via the catheter 603 before, during, and/or after supplying electrical energy to the first electrode via the current generator 20. In some embodiments, the electrical signals can continue to be applied while the catheter 603 and attached clot material CM are retracted proximally through the vessel V towards the catheter 604. In some embodiments, the current generator 20 can cease to supply electrical signals to the first electrode, while negative pressure can continue to be supplied to the catheter 603.

In FIG. 6B, the clot material CM has been moved to at least partially enter the catheter 603. In some embodiments, the clot material CM can substantially block the lumen of the catheter 603, thereby creating a "corking" effect that may be noticeable to a clinician supplying negative pressure to the catheter 603. Once the catheter 603 is corked with the clot material CM, it becomes increasingly difficult to supply continued negative pressure to the catheter 603. This corking effect can indicate to a clinician that the clot material CM has been engaged by the catheter 603 and that the clot material CM and catheter 603 can be retracted through the vessel V and into the catheter 604 or other surrounding catheter. In some embodiments, the current generator 20 can continue to supply electrical signals to the catheter 603 and the return electrode during retraction, while in other embodiments the current generator 20 can cease supplying electrical signals during retraction of the catheter 603 and the clot material CM.

IV. Select Embodiments of Waveforms for Electrically Enhanced Retrieval

FIGS. 7A-7E show various electrical waveforms for use with the treatment systems of the present technology. Although the waveforms and other power delivery parameters disclosed herein can be used with the devices and methods described above with respect to FIGS. 1A-6B, the waveforms and other parameters are also applicable to other device configurations and techniques. For example, the return electrode can be provided along the catheter wall, as a separate conductive member extending within the catheter lumen, as a needle electrode provided elsewhere in the body, etc. In each of these device configurations, the power delivery parameters and waveforms can be beneficially employed to promote clot adhesion without damaging surrounding tissue. Additionally, although the waveforms and other power delivery parameters disclosed herein may be used for treating a cerebral or intracranial embolism, other applications and other embodiments in addition to those described herein are within the scope of the technology. For example, the waveforms and power delivery parameters disclosed herein may be used to electrically enhance removal of emboli from body lumens other than blood vessels (e.g., the digestive tract, etc.) and/or may be used to electrically enhance removal of emboli from blood vessels outside of the brain (e.g., pulmonary blood vessels, blood vessels within the legs, etc.).

Figure 7A:
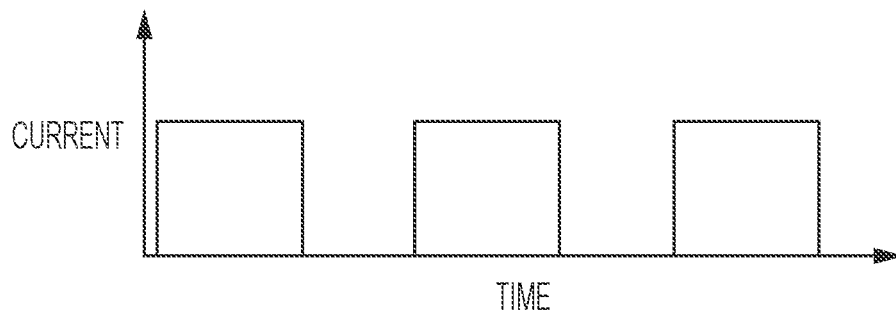
FIGS. 7A-7E illustrate sample waveforms for electrically enhanced removal of material from vessel lumens in accordance with one or more embodiments of the present disclosure.
Figure 7B:
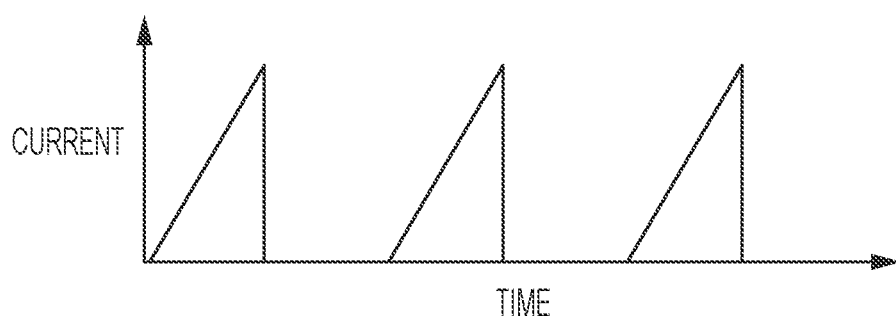
Figure 7C:
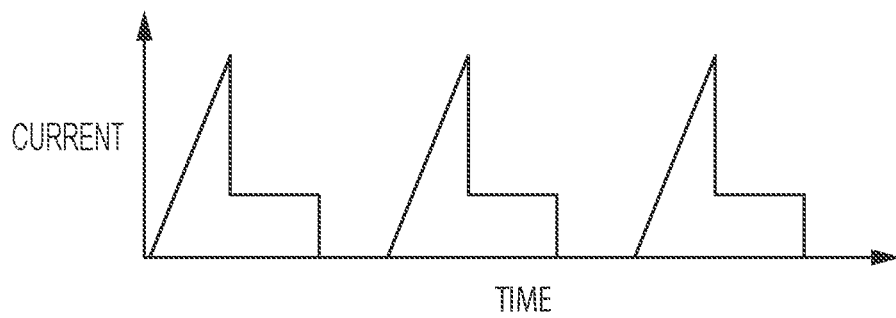
Figure 7D:
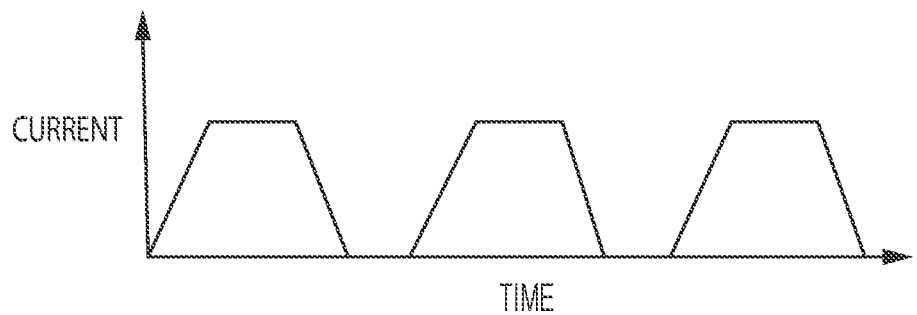
Figure 7E:
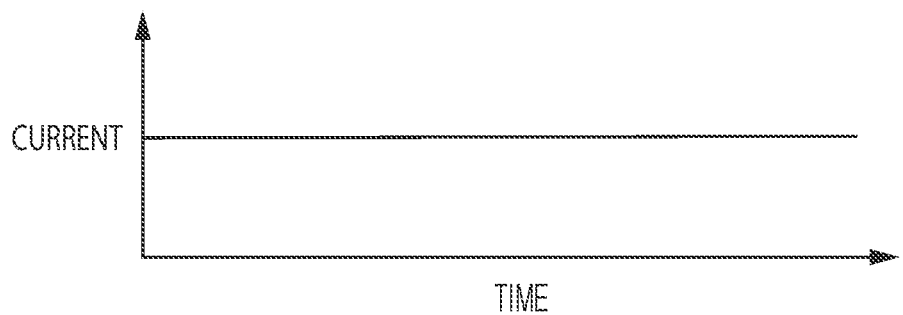

While applying a continuous uniform direct current (DC) electrical signal (as shown in FIG. 7E) to positively charge the interventional element and/or aspiration catheter can improve attachment to the thrombus, this can risk damage to surrounding tissue (e.g., ablation), and sustained current at a relatively high level may also be thrombogenic (i.e., may generate new clots). For achieving effective clot-grabbing without ablating tissue or generating substantial new clots at the treatment site, periodic waveforms have been found to be particularly useful. Without wishing to be bound by theory, the clot-adhesion effect appears to be most closely related to the peak current of the delivered electrical signal. Periodic waveforms can advantageously provide the desired peak current without delivering excessive total energy or total electrical charge. Periodic, non-square waveforms in particular are well suited to deliver a desired peak current while reducing the amount of overall delivered energy or charge as compared to either uniform applied current or square waveforms.

FIGS. 7A-7D illustrate various periodic waveforms that can be used with the devices and methods described above with respect to FIGS. 1A-6B, as well as with other devices and techniques. FIG. 7E illustrates a continuous uniform DC electrical signal which can also be used in some embodiments. Referring to FIGS. 7A-7D, electrical power can be delivered according to these waveforms as pulsed direct current. FIGS. 7A and 7B illustrate periodic square and triangular waveforms, respectively. These two waveforms have the same amplitude, but the triangular waveform is able to deliver the same peak current as the square waveform, with only half of the total charge delivered, and less total energy delivered. FIG. 7C illustrates another pulsed-DC or periodic waveform which is a composite of a square waveform and a triangular waveform. This superposition of a triangular waveform and a square waveform shown in FIG. 7C delivers additional efficacy compared to the triangular waveform of FIG. 7B while nonetheless delivering less overall energy than the square waveform of FIG. 7A. This is because the delivered energy is proportional to the square of current and the brief high peak in the composite waveform of FIG. 7C ensures that current is supplied without dispensing excessive energy. FIG. 7D illustrates yet another non-square waveform, in this case a trapezoidal waveform in which "ramp-up" and "ramp-down" portions at the beginning and end of each pulse provide periods of reduced current compared to square waveforms. In other embodiments, different non-square waveforms can be used, including a superposition of a square waveform with any non-square waveform, depending on the desired power delivery characteristics.

The waveform shape (e.g., pulse width, duty cycle, amplitude) and length of time can each be selected to achieve desired power delivery parameters, such as overall electrical charge, total energy, and peak current delivered to the interventional element and/or catheter. In some embodiments, the overall electrical charge delivered to the interventional element and/or catheter can be between about 30-1200 mC, or between about 120-600 mC. According to some embodiments, the total electrical charge delivered to the interventional element and/or catheter may be less than 600 mC, less than 500 mC, less than 400 mC, less than 300 mC, less than 200 mC, or less than 100 mC.

In some embodiments, the total energy delivered to the interventional element and/or aspiration catheter can be between about 0.75-24,000 mJ, or between about 120-24,000 mJ, or between about 120-5000 mJ. According to some embodiments, the total energy delivered to the interventional element and/or aspiration catheter may be less than 24,000 mJ, less than 20,000 mJ, less than 15,000 mJ, less than 10,000 mJ, less than 5,000 mJ, less than 4,000 mJ, less than 3,000 mJ, less than 2000 mJ, less than 1,000 mJ, less than 900 mJ, less than 800 mJ, less than 700 mJ, less than 600 mJ, less than 500 mJ, less than 400 mJ, less than 300 mJ, or less than 200 mJ, or less than 120 mJ, or less than 60 mJ, or less than 48 mJ, or less than 30 mJ, or less than 12 mJ, or less than 6 mJ, or less than 1.5 mJ.

In some embodiments, the peak current delivered can be between about 0.5-20 mA, or between about 0.5-5 mA. According to some embodiments, the peak current delivered may be greater than 0.5 mA, greater than 1 mA, greater than 1.5 mA, greater than 2 mA, greater than 2.5 mA, or greater than 3 mA.

The duration of power delivery is another important parameter that can be controlled to achieve the desired clot-adhesion effects without damaging tissue at the treatment site or generating new clots. In at least some embodiments, the total energy delivery time can be no more than 1 minute, no more than 2 minutes, no more than 3 minutes, no more than 4 minutes, or no more than 5 minutes. According to some embodiments, the total energy delivery time may be less about 30 seconds, less than about 1 minute, less than about 90 seconds, or less than about 2 minutes. As used herein, the "total energy delivery time" refers to the time period during which the waveform is supplied to the interventional element and/or catheter (including those periods of time between pulses of current).

The duty cycle of the applied electrical signal can also be selected to achieve the desired clot-adhesion characteristics without ablating tissue or promoting new clot formation. In some embodiments, the duty cycle can be between about 5% about 99% or between about 5% to about 20%. According to some embodiments, the duty cycle may be about 10%, about 20%, about 30%, about 40%, or about 50%. In yet other embodiments, a constant current may be used, in which the duty cycle is 100%. For 100% duty cycle embodiments, a lower time or current may be used to avoid delivering excess total energy to the treatment site.

Table 1 presents a range of values for power delivery parameters of different waveforms. For each of the conditions set forth in Table 1, a resistance of 1 kohm and a frequency of 1 kHz (for the Square, Triangle, and Composite conditions) was used. The Constant conditions represent a continuous and steady current applied for the duration, i.e. 100% duty cycle. The Peak Current 1 column represents the peak current for the corresponding waveform. For the Composite conditions, the Peak Current 2 column indicates the peak current of the second portion of the waveform. For example, referring back to FIG. 7C, Peak Current 1 would correspond to the current at the top of the triangular portion of the waveform, while Peak Current 2 would correspond to the current at the top of the square portion of the waveform.

TABLE 1

| Condition | Peak Current 1 (mA) | Peak Current 2 (mA) | Duty Cycle 1 (%) | Duty Cycle 2 (%) | Peak Voltage (V) | Pulse Width (ms) | Total Time (s) | Total Charge (mC) | Total Energy (@ R = 1000 ohm) (mJ) | Total Energy (@ R = 50 ohm) (mJ) |
|---|---|---|---|---|---|---|---|---|---|---|
| Constant 1 | 2 | 0 | 100 | 0 | 2 | n/a | 120 | 240 | 480 | 24 |
| Constant 2 | 2 | 0 | 100 | 0 | 2 | n/a | 60 | 120 | 240 | 12 |
| Constant 3 | 10 | 0 | 100 | 0 | 10 | n/a | 60 | 600 | 6000 | 300 |
| Constant 4 | 20 | 0 | 100 | 0 | 20 | n/a | 60 | 1200 | 24000 | 1200 |
| Constant 5 | 10 | 0 | 100 | 0 | 10 | n/a | 120 | 1200 | 12000 | 600 |
| Constant 6 | 1 | 0 | 100 | 0 | 1 | n/a | 120 | 120 | 120 | 6 |
| Constant 7 | 0.5 | 0 | 100 | 0 | 1 | n/a | 120 | 60 | 30 | 1.5 |

TABLE 1-continued

| Condition | Peak Current 1 (mA) | Peak Current 2 (mA) | Duty Cycle 1 (%) | Duty Cycle 2 (%) | Peak Voltage (V) | Pulse Width (ms) | Total Time (s) | Total Charge (mC) | Total Energy (@ R = 1000 ohm) (mJ) | Total Energy (@ R = 50 ohm) (mJ) |
|---|---|---|---|---|---|---|---|---|---|---|
| Constant 8 | 0.5 | 0 | 100 | 0 | 1 | n/a | 60 | 30 | 15 | 0.75 |
| Square 1 | 10 | 0 | 10 | 0 | 10 | 0.1 | 120 | 120 | 1200 | 60 |
| Square 2 | 4 | 0 | 50 | 0 | 4 | 0.5 | 120 | 240 | 960 | 48 |
| Square 3 | 20 | 0 | 10 | 0 | 20 | 0.1 | 120 | 240 | 4800 | 240 |
| Square 4 | 20 | 0 | 10 | 0 | 20 | 0.1 | 60 | 120 | 2400 | 120 |
| Square 5 | 10 | 0 | 10 | 0 | 10 | 0.1 | 60 | 60 | 600 | 30 |
| Triangle 1 | 10 | 0 | 10 | 0 | 10 | 0.1 | 120 | 60 | 1200 | 60 |
| Triangle 2 | 20 | 0 | 10 | 0 | 20 | 0.1 | 120 | 120 | 4800 | 240 |
| Composite 1 | 20 | 1 | 10 | 20 | 20 | 0.3 | 120 | 144 | 4824 | 264 |
| Composite 2 | 10 | 2 | 10 | 20 | 10 | 0.3 | 120 | 108 | 1296 | 156 |

As seen in Table 1, the periodic waveforms (Square, Triangle, and Composite conditions) achieve higher peak currents with lower overall charge delivered than the corresponding Constant conditions. For example, in condition Constant 4, a peak current of 20 mA corresponds to a total energy delivered of 24,000 mJ, while condition Square 3 delivers a peak current of 20 mA with a total energy of only 4,800 mJ. Conditions Triangle 2 and Composite 1 similarly deliver lower total energy while maintaining a peak current of 20 mA. Since clot-adhesion appears to be driven by peak current, these periodic waveforms can therefore offer improved clot adhesion while reducing the risk of damaging tissue at the treatment site or promoting new clot formation. Table 1 also indicates that the Triangle and Composite conditions achieve higher peak currents with lower overall charge delivered than the corresponding Square conditions. For example, condition Square 3 has a peak current of 20 mA and a total charge delivered of 240 mC, while condition Triangle 2 has a peak current of 20 mA but a total charge delivered of only 120 mC, and condition Composite 1 has a peak current of 20 mA and a total charge delivered of only 144 mC. As such, these non-square waveforms provide additional benefits by delivering desirable peak current while reducing the overall charge delivered to the treatment site.

Although Table 1 represents a series of waveforms with a single frequency (1 kHz), in some embodiments the frequency of the pulsed-DC waveforms can be controlled to achieve the desired effects. For example, in some embodiments the frequency of the waveform can be between 1 Hz and 1 MHz, between 1 Hz and 1 kHz, or between 500 Hz to 1 kHz.

V. CONCLUSION

This disclosure is not intended to be exhaustive or to limit the present technology to the precise forms disclosed herein. Although specific embodiments are disclosed herein for illustrative purposes, various equivalent modifications are possible without deviating from the present technology, as those of ordinary skill in the relevant art will recognize. In some cases, well-known structures and functions have not been shown and/or described in detail to avoid unnecessarily obscuring the description of the embodiments of the present technology. Although steps of methods may be presented herein in a particular order, in alternative embodiments the steps may have another suitable order. Similarly, certain aspects of the present technology disclosed in the context of particular embodiments can be combined or eliminated in other embodiments. Furthermore, while advantages associated with certain embodiments may have been disclosed in the context of those embodiments, other embodiments can also exhibit such advantages, and not all embodiments need necessarily exhibit such advantages or other advantages disclosed herein to fall within the scope of the present technology. Accordingly, this disclosure and associated technology can encompass other embodiments not expressly shown and/or described herein.

Throughout this disclosure, the singular terms "a," "an," and "the" include plural referents unless the context clearly indicates otherwise. Similarly, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the terms "comprising" and the like are used throughout this disclosure to mean including at least the recited feature(s) such that any greater number of the same feature(s) and/or one or more additional types of features are not precluded. Directional terms, such as "upper," "lower," "front," "back," "vertical," and "horizontal," may be used herein to express and clarify the relationship between various elements. It should be understood that such terms do not denote absolute orientation. Reference herein to "one embodiment," "an embodiment," or similar formulations means that a particular feature, structure, operation, or characteristic described in connection with the embodiment can be included in at least one embodiment of the present technology. Thus, the appearances of such phrases or formulations herein are not necessarily all referring to the same embodiment. Furthermore, various particular features, structures, operations, or characteristics may be combined in any suitable manner in one or more embodiments.

We claim:

1. A method for electrically enhanced thrombectomy, the method comprising:
    disposing a distal portion of a catheter adjacent to a treatment site in the body, the catheter comprising a first electrode disposed in the distal portion and coupled to a first electrical terminal of a power supply, and a second electrode comprising an expandable member extending around an outer surface of the catheter;
    supplying electric current to the first electrical terminal; and
    supplying negative pressure through the catheter to aspirate a region adjacent to the treatment site.

2. The method of claim 1, wherein the second electrode is disposed at a position spaced apart from the first electrode, the second electrode coupled to a second electrical terminal of the power supply.

3. The method of claim 2, wherein the first electrical terminal is positive, and wherein the second electrical terminal is negative.

4. The method of claim 2, wherein the second electrode comprises a conductive element disposed in the distal portion of the catheter.

5. The method of claim 1, further comprising supplying the electric current to the first electrical terminal while supplying the negative pressure through the catheter.

6. The method of claim 1, further comprising ceasing the supplying of electric current to the first electrical terminal after a first time period.

7. The method of claim 6, wherein the first time period is less than about 5 minutes.

8. The method of claim 6, wherein the first time period is less than about 2 minutes.

9. The method of claim 1, wherein the first electrode is coupled to the first electrical terminal via a conductive lead extending proximally along the catheter.

10. The method of claim 1, wherein the first electrode comprises a conductive band extending at least partially circumferentially around the distal portion of the catheter.

11. The method of claim 10, wherein the conductive band is disposed on an inner surface of the catheter.

12. The method of claim 10, wherein the conductive band is disposed on an outer surface of the catheter.

13. The method of claim 1, wherein the treatment site in the body is proximate to or adjacent to a thrombus in a blood vessel.

14. A method, comprising:
 disposing a distal portion of a catheter adjacent to a thrombus within a vessel, the catheter comprising:
  a lumen having a distal opening; and
  a first electrode coupled to a distal portion in electrical communication with an extracorporeal power supply, and a second electrode comprising a conductive element extending around an outer surface of the catheter;
 supplying negative pressure through the catheter lumen to draw at least a portion of the thrombus into the catheter lumen; and
 while supplying the negative pressure, supplying positive electrical current to the first electrode to promote attraction between the thrombus and the first electrode.

15. The method of claim 14, wherein the second electrode is disposed at a position spaced apart from the first electrode, the second electrode in electrical communication with the extracorporeal power supply.

* * * * *